(12) United States Patent
Touge et al.

(10) Patent No.: US 9,073,827 B2
(45) Date of Patent: Jul. 7, 2015

(54) METHOD FOR PRODUCING DIAMINE COMPOUND

(75) Inventors: Taichiro Touge, Hiratsuka (JP);
Tomohiko Hakamata, Hamamatsu (JP);
Hideki Nara, Fujisawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/111,828

(22) PCT Filed: Apr. 27, 2012

(86) PCT No.: PCT/JP2012/061445
§ 371 (c)(1),
(2), (4) Date: Oct. 15, 2013

(87) PCT Pub. No.: WO2012/147944
PCT Pub. Date: Nov. 1, 2012

(65) Prior Publication Data
US 2014/0039220 A1 Feb. 6, 2014

(30) Foreign Application Priority Data
Apr. 28, 2011 (JP) ................. 2011-101528

(51) Int. Cl.
C07C 303/40 (2006.01)
C07C 311/05 (2006.01)
C07C 311/18 (2006.01)
C07C 309/73 (2006.01)

(52) U.S. Cl.
CPC ........... *C07C 303/40* (2013.01); *C07C 2101/16* (2013.01); *C07C 311/05* (2013.01); *C07C 311/18* (2013.01); *C07C 309/73* (2013.01)

(58) Field of Classification Search
CPC .. C07C 303/40; C07C 309/73; C07C 311/05; C07C 311/18; C07C 2101/16
USPC ..................................................... 564/92, 99
See application file for complete search history.

(56) References Cited

U.S. PATENT DOCUMENTS

| 7,964,744 | B2 | 6/2011 | Nara et al. |
| 8,044,224 | B2 | 10/2011 | Carreira |
| 2010/0016618 | A1 | 1/2010 | Carreira |
| 2010/0076210 | A1 | 3/2010 | Nara et al. |
| 2011/0021500 | A1* | 1/2011 | Gottschling et al. ..... 514/212.02 |
| 2012/0123142 | A1 | 5/2012 | Dyke et al. |
| 2013/0158276 | A1 | 6/2013 | Touge et al. |

FOREIGN PATENT DOCUMENTS

| CN | 101652376 A | 2/2010 |
| CN | 101676294 A | 3/2010 |
| JP | 2012-67071 A | 4/2012 |
| WO | 2007147897 A1 | 12/2007 |

(Continued)

OTHER PUBLICATIONS

Handbook of Chemistry and Physics, 9th Edition, 2014-2015, p. 3-210.*
State Intellectual Property Office of the P.R.C., Communication dated Jun. 13, 2014, issued in corresponding Chinese application No. 201280020119.4.
Grazia Zassinovich et al., "Asymmetric Hydrogen Transfer Reactions Promoted by Homogeneous Transition Metal Catalysts", Chem. Rev. 1992, pp. 1051-1069, vol. 92.

(Continued)

*Primary Examiner* — Paul A Zucker
*Assistant Examiner* — Mark Luderer
(74) *Attorney, Agent, or Firm* — Sughrue Mion, PLLC

(57) ABSTRACT

The present invention provides a method for producing a compound represented by general formula (1) (wherein $R^1$, $R^2$, $R^3$, $R^{10}$-$R^{14}$, $A^1$-$A^3$, $n_1$ and $n_2$ are as defined in the description), which is characterized by reacting a compound represented by general formula (2) (wherein $R^{10}$-$R^{14}$, $A^1$-$A^3$, $n_1$, $n_2$ and B are as defined in the description) with a diamine compound represented by general formula (3) (wherein $R^1$-$R^3$ are as defined in the description). The present invention is a method for producing a diamine compound, which is useful for the formation of a ruthenium-diamine complex, under mild conditions, said method being able to be put in industrial practice.

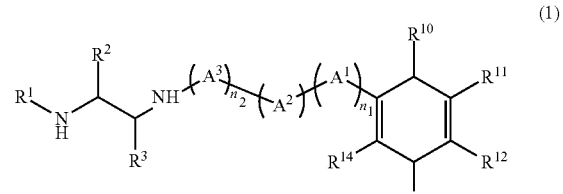

(1)

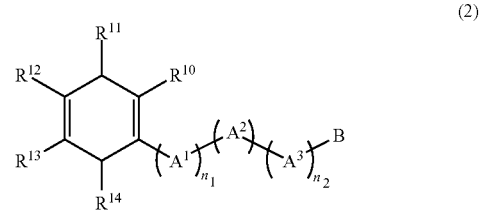

(2)

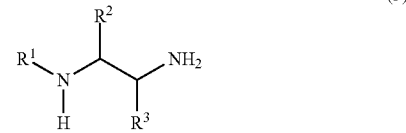

(3)

3 Claims, No Drawings

(56) References Cited

FOREIGN PATENT DOCUMENTS

| | | | |
|---|---|---|---|
| WO | 2010106364 A2 | 9/2010 | |
| WO | WO2010106364 | * 9/2010 | ............... B01J 23/46 |

OTHER PUBLICATIONS

Shohei Hashiguchi et al., "Asymmetric Transfer Hydrogenation of Aromatic Ketones Catalyzed by Chiral Ruthenium(II) Complexes", J. Am. Chem. Soc. 1995, pp. 7562-7563, vol. 117.

Akio Fujii et al., "Ruthemium(II)-Catalyzed Asymmetric Transfer Hydrogenation of Ketones Using a Formic Acid-Triethylamine Mixture", J. Am. Chem. Soc. 1996, pp. 2521-2522, vol. 118.

Nobuyuki Uematsu et al., "Asymmetric Transfer Hydrogenation of Imines", J. Am. Chem. Soc. 1996, pp. 4916-4917.

Aidan M. Hayes et al., "A Class of Ruthenium(II) Catalyst for Asymmetric Transfer Hydrogenations of Ketones", J. Am. Chem. Soc. 2005, pp. 7318-7319, vol. 127.

David J. Morris et al., "The 'Reverse-Tethered' Ruthenium(II) Catalyst for Asymmetric Transfer Hydrogenation: Further Applications", J. Org. Chem. 2006, pp. 7035-7044, vol. 71.

Fung Kei Cheung et al., "The use of a [4+2] cycloaddition reaction for the preparation of a series of 'tethered' Ru(II)-diamine and aminoalcohol complexes", Org. Biomol. Chem. 2007, pp. 1093-1103, vol. 5.

Fung Kei (Kathy) Cheung et al., "Kinetic and structural studies on 'tethered' Ru(II) arene ketone reduction catalysts", Dalton Trans. 2010, pp. 1395-1402, vol. 39.

Fung K. Cheung et al., "An Investigation into the Tether Length and Substitution Pattern of Arene-Substituted Complexes for Asymmetric Transfer Hydrogenation of Ketones", Organic Letters 2007, pp. 4659-4662, vol. 9, No. 22.

Jose E.D. Martins et al., "Further 'tethered' Ru(II) catalysts for asymmetric transfer hydrogenation (ATH) of ketones; the use of a benzylic linker and a cyclohexyldiamine ligand", Journal of Organometallic Chemistry 2008, pp. 3527-3532, vol. 693.

International Searching Authority International Search Report for PCT/JP2012/061445 dated Jul. 3, 2012.

* cited by examiner

METHOD FOR PRODUCING DIAMINE COMPOUND

CROSS REFERENCE TO RELATED APPLICATIONS

This application is a National Stage of International Application No. PCT/JP2012/061445 filed Apr. 27, 2012, claiming priority based on Japanese Patent Application No. 2011-101528 filed Apr. 28, 2011, the contents of all of which are incorporated herein by reference in their entirety.

TECHNICAL FIELD

The present invention relates to a method for producing a diamine compound useful for forming a ruthenium-diamine complex important as an asymmetric reduction catalyst.

BACKGROUND ART

Many asymmetric reactions including asymmetric reduction have been developed, and many asymmetric reactions have been reported in which asymmetric metal complexes having optically active phosphine ligands are used. On the other hand, many reports have shown that complexes in which optically active nitrogen compounds are coordinated to transition metals, such as ruthenium, rhodium, and iridium, for example, have excellent performances as catalysts for asymmetric synthesis reactions. Moreover, to enhance the performances of these catalysts, various optically active nitrogen compounds have been developed (Non Patent Literatures 1, 2, 3, 4, etc.). In particular, M. Wills et al. have reported that complexes in which a diamine moiety and an aromatic ring (arene) moiety coordinated to the ruthenium metal are linked by a carbon chain exhibit higher activities than conventional catalysts (Non Patent Literatures 5, 6, 7, 8, 9, 10, etc.).

CITATION LIST

Non Patent Literatures

Non Patent Literature 1: Chem. Rev. (1992) p. 1051
Non Patent Literature 2: J. Am. Chem. Soc. 117 (1995) p. 7562
Non Patent Literature 3: J. Am. Chem. Soc. 118 (1996) p. 2521
Non Patent Literature 4: J. Am. Chem. Soc. 118 (1996) p. 4916
Non Patent Literature 5: J. Am. Chem. Soc. 127 (2005) p. 7318
Non Patent Literature 6: J. Org. Chem. 71 (2006) p. 7035
Non Patent Literature 7: Org. Biomol. Chem. 5 (2007) p. 1093
Non Patent Literature 8: Org. Lett. 9 (2007) p. 4659
Non Patent Literature 9: J. Organometallic. Chem. 693 (2008) p. 3527
Non Patent Literature 10: Dalton. Trans. 39 (2010) p. 1395

SUMMARY OF INVENTION

However, these complexes have the following problems. Specifically, these complexes are produced through hazardous processes such as the Birch reduction of an alcohol having an aromatic ring, the subsequent conversion to an aldehyde under a low temperature of −80° C., and the subsequent synthesis using pyrophoric $NaBH_4$ or $LiAlH_4$. Moreover, the yields of these complexes are low.

To solve the above problems, the present inventors have developed a production method which is performed under mild conditions and hence can be carried out industrially.

Specifically, the present invention includes the following contents.

[1] A method for producing a compound represented by the following general formula (1):

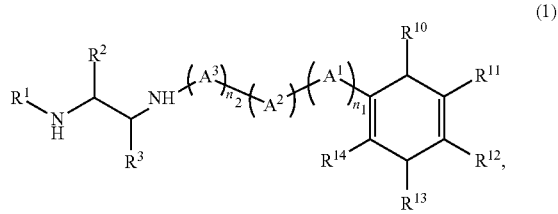

wherein $R^1$ represents an alkyl group having 1 to 10 carbon atoms; an alkanesulfonyl group having 1 to 10 carbon atoms and optionally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to carbon atoms in total; or a benzoyl group optionally substituted with an alkyl group having 1 to 10 carbon atoms, $R^2$ and $R^3$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trisubstituted alkylsilyl group, $A^1$ and $A^3$ represent methylene, $A^2$ represents an oxygen atom or methylene, and $n_1$ and $n_2$ are each independently 1 to 3, the method comprising:

reacting a compound represented by the following general formula (2):

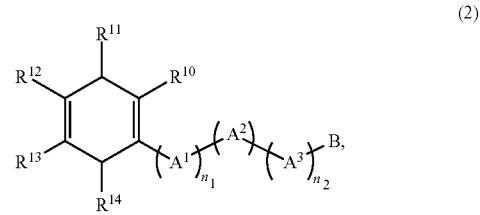

wherein $R^{10}$ to $R^{14}$, $A^1$ to $A^3$, $n_1$, and $n_2$ are the same as those defined in the general formula (1), and B represents a halogen atom, an alkanesulfonyloxy group, or an arenesulfonyloxy group, with a diamine compound represented by the following general formula (3):

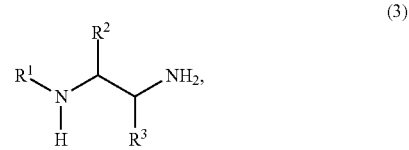

wherein $R^1$ to $R^3$ are the same as those defined in the general formula (1).

[2] The production method according to [1], wherein the compound represented by the general formula (2) is reacted with the diamine compound represented by the general formula (3) at a temperature of 100° C. to 200° C.

[3] A compound represented by the following general formula (2):

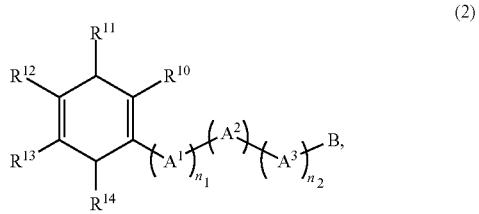

(2)

wherein $R^{10}$ to $R^{14}$ each independently represent a hydrogen atom, an alkyl group having 1 to 10 carbon atoms, an alkoxy group having 1 to 10 carbon atoms, or a trisubstituted alkylsilyl group, $A^1$ and $A^3$ represent methylene, $A^2$ represents an oxygen atom or methylene, B represents a halogen atom, an alkanesulfonyloxy group, or an arenesulfonyloxy group, and $n_1$ and $n_2$ are each independently 1 to 3.

The present invention provides a method for producing a diamine compound in which a diamine moiety and an arene moiety to be coordinated to a ruthenium metal are linked by a carbon chain. The above-described conventional methods for producing a diamine compound have the following problems: the complexity of the synthesis method; the use of the Birch reduction which necessitates the use of toxic ammonia gas and an ultra low-temperature apparatus; the inevitable use of the Swern oxidation which causes problems, in industrial application, associated with the odor of by-produced dimethyl sulfide, the hazardous nature of carbon monoxide, the need for a cryogenic reactor, and the like; low yields in some reactions; and the like. In contrast, the present invention makes it possible to simply and efficiently produce a highly active ruthenium-diamine complex by the production method which uses a novel intermediate obtained by halogenating or sulfonylating an alcohol synthesized by the Diels-Alder reaction.

DESCRIPTION OF EMBODIMENTS

Hereinafter, the present invention will be described in further detail.

In the present invention, a compound represented by the following general formula (1) is produced by reacting a compound represented by the following general formula (2) with a diamine compound represented by the following general formula (3):

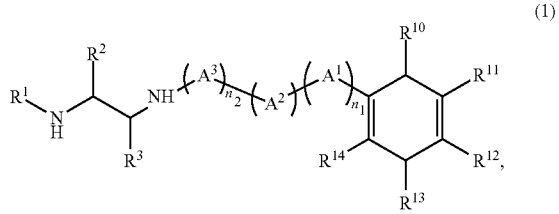

(1)

wherein $R^1$ represents an alkyl group having 1 to 10 carbon atoms; an alkanesulfonyl group having 1 to 10 carbon atoms and optionally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to 11 carbon atoms in total; or a benzoyl group optionally substituted with an alkyl group having 1 to 10 carbon atoms, $R^2$ and $R^3$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trisubstituted alkylsilyl group, $A^1$ and $A^3$ represent methylene, $A^2$ represents an oxygen atom or methylene, and $n_1$ and $n_2$ are each independently 1 to 3,

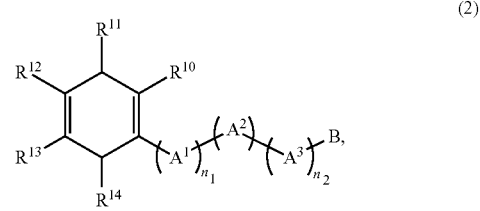

(2)

wherein $R^{10}$ to $R^{14}$, $A^1$ to $A^3$, $n_1$ and $n_2$ are the same as those defined in the general formula (1), and B represents a halogen atom, an alkanesulfonyloxy group, or an arenesulfonyloxy group, and

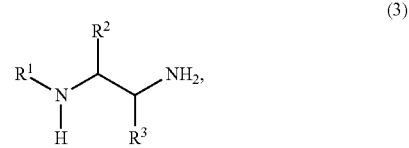

(3)

wherein $R^1$ to $R^3$ are the same as those defined in the general formula (1).

The alkyl group having 1 to 10 carbon atoms represented by $R^1$ is a linear or branched alkyl group having 1 to 10 carbon atoms, and preferably having 1 to 5 carbon atoms. Specific examples of the alkyl group include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group, a n-decyl group, and the like.

The alkanesulfonyl group having 1 to 10 carbon atoms represented by $R^1$ includes a methanesulfonyl group, an ethanesulfonyl group, a propanesulfonyl group, and the like. The alkanesulfonyl group is optionally substituted with one or multiple halogen atoms. The halogen atom includes chlorine atoms, bromine atoms, fluorine atoms, and the like. The alkanesulfonyl group having 1 to 10 carbon atoms and substituted with a halogen atom includes a trifluoromethanesulfonyl group and the like.

The arenesulfonyl group represented by $R^1$ includes a benzenesulfonyl group and the like. The arenesulfonyl group is optionally substituted with one or multiple alkyl groups having 1 to 10 carbon atoms, halogenated alkyl groups having 1 to 10 carbon atoms, or halogen atoms. The alkyl group having 1 to 10 carbon atoms includes those listed as the alkyl group having 1 to 10 carbon atoms represented by $R^1$, and the like. The halogenated alkyl group having 1 to 10 carbon atoms includes halides (the halogen atom includes a chlorine atom, a bromine atom, a fluorine atom, and the like) of those listed as the alkyl group having 1 to 10 carbon atoms represented by $R^1$, and the like. The halogen atom includes a chlorine atom, a bromine atom, a fluorine atom, and the like. The arenesulfonyl group substituted with an alkyl group having 1 to 10 carbon atoms, a halogenated alkyl group having 1 to 10 carbon atoms, or a halogen atom includes a p-toluenesulfonyl group, a 2,4,6-trimethylbenzenesulfonyl group, a 4-trifluoromethylbenzenesulfonyl group, a pentafluorobenzenesulfonyl group, and the like.

The alkoxycarbonyl group having 2 to 11 carbon atoms in total represented by $R^1$ is a linear or branched alkoxycarbonyl group having 2 to 11 carbon atoms in total, and preferably having 2 to 5 carbon atoms in total. Specific examples of the alkoxycarbonyl group include a methoxycarbonyl group, an ethoxycarbonyl group, a t-butoxycarbonyl group, and the like.

The benzoyl group represented by $R^1$ is optionally substituted with one or multiple alkyl groups having 1 to 10 carbon atoms. The alkyl group having 1 to 10 carbon atoms includes those listed as the alkyl group having 1 to 10 carbon atoms represented by $R^1$, and the like. The benzoyl group optionally substituted with an alkyl group having 1 to 10 carbon atoms includes a benzoyl group, a p-toluoyl group, an o-toluoyl group, and the like.

The alkyl group having 1 to 10 carbon atoms represented by each of $R^2$ and $R^3$ includes those listed as the alkyl group having 1 to 10 carbon atoms represented by $R^1$, and the like.

The phenyl group represented by each of $R^2$ and $R^3$ is optionally substituted with one or multiple alkyl groups having 1 to 10 carbon atoms, alkoxy groups having 1 to 10 carbon atoms, or halogen atoms. The alkyl group having 1 to 10 carbon atoms includes those listed as the alkyl group having 1 to 10 carbon atoms represented by $R^1$, and the like. The alkoxy groups having 1 to 10 carbon atoms are each a linear or branched alkoxy group having 1 to 10 carbon atoms, and preferably having 1 to 5 carbon atoms. Specific examples of the alkoxy group include a methoxy group, an ethoxy group, a n-propoxy group, an isopropoxy group, a n-butoxy group, an isobutoxy group, a s-butoxy group, a t-butoxy group, a n-pentyloxy group, a n-hexyloxy group, a n-heptyloxy group, a n-octyloxy group, a n-nonyloxy group, a n-decyloxy group, and the like. The halogen atom includes a chlorine atom, a bromine atom, a fluorine atom, and the like. The phenyl group substituted with an alkyl group having 1 to 10 carbon atoms, an alkoxy group having 1 to 10 carbon atoms, or a halogen atom includes a 2,4,6-trimethylphenyl group, a 4-methoxyphenyl group, a 2,4,6-trimethoxyphenyl group, a 4-fluorophenyl group, a 2-chlorophenyl group, a 4-chlorophenyl group, a 2,4-dichlorophenyl group, and the like.

The cycloalkyl group having 3 to 8 carbon atoms represented by each of $R^2$ and $R^3$ is a monocyclic, polycyclic, or cross-linked cycloalkyl group having 3 to 8 carbon atoms, and preferably having 5 to 8 carbon atoms. Specific examples of the cycloalkyl group having 3 to 8 carbon atoms include a cyclopropyl group, a cyclobutyl group, a cyclopentyl group, a cyclohexyl group, a cycloheptyl group, a cyclooctyl group, and the like.

These cycloalkyl groups are optionally substituted with alkyl groups such as methyl groups, isopropyl groups, and t-butyl groups; or the like.

Regarding the ring formed by $R^2$ and $R^3$ together, $R^2$ and $R^3$ together form a linear or branched alkylene group having 2 to 10 carbon atoms, and preferably 3 to 10 carbon atoms, and thus form a preferably 4- to 8-membered, more preferably 5- to 8-membered, cycloalkane ring together with the adjacent carbon atoms. Preferred examples of the cycloalkane ring include a cyclopentane ring, a cyclohexane ring, and a cycloheptane ring. These rings may have, as substituents, alkyl groups such as methyl groups, isopropyl groups, and t-butyl groups, and the like.

The alkyl group having 1 to 10 carbon atoms represented by each of $R^{10}$ to $R^{14}$ is a linear or branched alkyl group having 1 to 10 carbon atoms, and preferably having 1 to 5 carbon atoms. Specific examples of the alkyl group include a methyl group, an ethyl group, a n-propyl group, an isopropyl group, a n-butyl group, an isobutyl group, a s-butyl group, a t-butyl group, a n-pentyl group, a n-hexyl group, a n-heptyl group, a n-octyl group, a n-nonyl group, a n-decyl group, and the like.

The alkoxy group having 1 to 10 carbon atoms represented by each of $R^{10}$ to $R^{14}$ is a linear or branched alkoxy group having 1 to 10 carbon atoms, and preferably having 1 to 5 carbon atoms. Specific examples of the alkoxy group include a methoxy group, an ethoxy group, a n-propoxy group, an isopropoxy group, a n-butoxy group, an isobutoxy group, a s-butoxy group, a t-butoxy group, a n-pentyloxy group, a n-hexyloxy group, a n-heptyloxy group, a n-octyloxy group, a n-nonyloxy group, a n-decyloxy group, and the like.

The alkyl groups of the trisubstituted alkylsilyl group represented by each of $R^{10}$ to $R^{14}$ are alkyl groups having 1 to 10 carbon atoms. Specific examples thereof include methyl groups, ethyl groups, n-propyl groups, isopropyl groups, n-butyl groups, isobutyl groups, s-butyl groups, t-butyl groups, n-pentyl groups, n-hexyl groups, n-heptyl groups, n-octyl groups, n-nonyl groups, n-decyl groups, and the like. Specific examples of the trisubstituted alkylsilyl group include a trimethylsilyl group, a triethylsilyl group, a t-butyldimethylsilyl group, a triisopropylsilyl group, and the like.

The halogen atom represented by B includes a chlorine atom, a bromine atom, an iodine atom, and the like.

The alkanesulfonyloxy group represented by B is preferably a linear or branched alkanesulfonyloxy group having 1 to 5 carbon atoms. Specific examples of the alkanesulfonyloxy group include a methanesulfonyloxy group, a trifluoromethanesulfonyl group, an ethanesulfonyloxy group, an isopropanesulfonyloxy group, a n-propylsulfonyloxy group, a n-butylsulfonyloxy group, a tert-butylsulfonyloxy group, a n-pentanesulfonyloxy group, and the like.

The arenesulfonyloxy group represented by B includes a phenylsulfonyloxy group, a naphthylsulfonyloxy group, and the like. The arenesulfonyloxy group may have 1 to 3 substituents on the phenyl ring of the phenylsulfonyloxy group or on the naphthalene ring of the naphthylsulfonyloxy group.

The substituents include linear or branched alkyl groups having 1 to 6 carbon atoms, linear or branched alkoxy groups having 1 to 6 carbon atoms, nitro groups, halogen atoms, and the like. Specific examples of the phenylsulfonyloxy group include phenylsulfonyloxy, 4-methylphenylsulfonyloxy, 2-methylphenylsulfonyloxy, 4-nitrophenylsulfonyloxy, 4-methoxyphenylsulfonyloxy, 2-nitrophenylsulfonyloxy, 3-chlorophenylsulfonyloxy, and the like. Specific examples of the naphthylsulfonyloxy group include α-naphthylsulfonyloxy and β-naphthylsulfonyloxy groups, and the like.

Subsequently, description is given of a step of obtaining the compound represented by the general formula (1) by reacting the compound represented by the general formula (2) with the diamine compound represented by the general formula (3) (Scheme 1).

Scheme 1

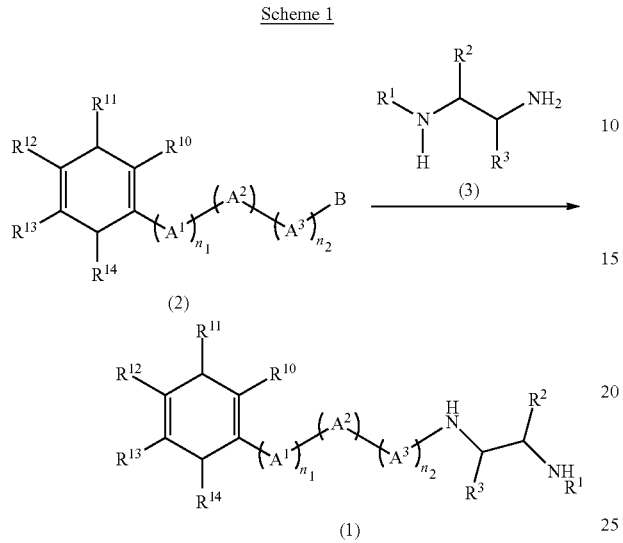

wherein $R^1$ to $R^3$, $R^{10}$ to $R^{14}$, $A^1$, $A^2$, $A^3$, $n_1$, $n_2$, and B are the same as described above.

A solvent used for synthesizing the compound represented by the general formula (1) from the compound represented by the general formula (2) and the compound of the general formula (3), which is a diamine compound, is preferably an aromatic hydrocarbon such as toluene, xylene, or mesitylene; a halogenated aromatic hydrocarbon such as chlorobenzene; an ether such as 1,4-dioxane; an aprotic polar solvent such as N,N-dimethylformamide or dimethyl sulfoxide, or the like, and is particularly preferably dimethyl sulfoxide, toluene, xylene, or mesitylene. In addition, the reaction can also be performed in a mixture of an organic solvent with water by using water as another solvent. Meanwhile, a base used for the reaction is preferably an inorganic base such as sodium hydroxide, sodium hydrogen carbonate, sodium carbonate, potassium hydroxide, potassium hydrogen carbonate, potassium carbonate, lithium hydroxide, lithium hydrogen carbonate, lithium carbonate, cesium carbonate, magnesium hydroxide, magnesium carbonate, calcium hydroxide, or calcium carbonate; or a tertiary organic amine such as trimethylamine, triethylamine, triisopropylamine, tributylamine, or diisopropylethylamine, and is particularly preferably triethylamine or diisopropylethylamine. The amount of the base used is 0.2 to 2.0 equivalents, and preferably 1.0 to 1.5 equivalents to the compound represented by the general formula (2). The reaction temperature is, for example, 100° C. to 200° C., and preferably 100° C. to 160° C. The reaction time is 30 minutes to 30 hours, and preferably 1 hour to 12 hours, although it varies depending on the reaction substrate used. The reaction is preferably performed in an inert gas such as nitrogen gas or argon gas. Moreover, an additive such as sodium iodide, potassium iodide, lithium iodide, sodium bromide, potassium bromide, lithium bromide, potassium chloride, or lithium chloride may be added. The additive is preferably potassium iodide or lithium iodide. The amount of the additive is 0 to 10 equivalents, and preferably 0.1 to 1 equivalents to the compound represented by the general formula (2).

The compound represented by the general formula (2) can be synthesized, for example, by a method described in Scheme 2 below.

Scheme 2

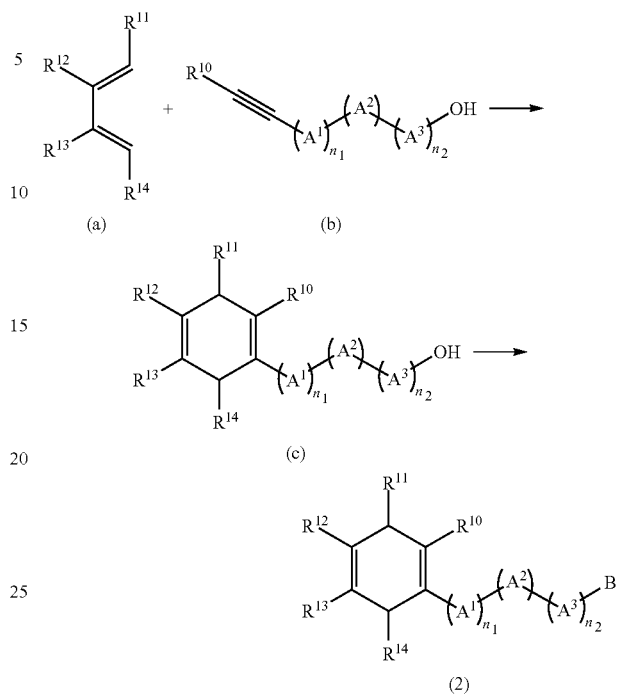

wherein $R^{10}$ to $R^{14}$, $A^1$, $A^2$, $A^3$, $n_1$, $n_2$, and B are the same as described above.

The alcohol (c) can be synthesized by the Diels-Alder reaction between the diene (a) having substituents and the alkyne (b) having a substituent. The reagent used includes metal complexes such as [1,2-bis(diphenylphosphino) ethane]cobalt(II) dibromide, 1,5-cyclooctadiene(naphthalene)rhodium(I) tetrafluoroborate, dichloro(1,4-diaza-1,3-diene)iron(II), and dichlorobis(tri-o-biphenylphosphite)nickel (II). A solvent used for the Diels-Alder reaction is not particularly limited, unless the reaction is adversely affected. The solvent includes ethers such as diethyl ether, tetrahydrofuran, and dioxane; aromatic hydrocarbons such as toluene and xylene; halogen-containing hydrocarbon solvents such as dichloromethane and 1,2-dichloroethane; aprotic polar solvents such as acetonitrile, ethyl acetate, and acetone; and the like. Dichloromethane or tetrahydrofuran is particularly preferable. Although the reaction temperature of the Diels-Alder reaction naturally varies depending on the substrate used, the reaction temperature is in a range of generally −20° C. to 100° C., and preferably 10° C. to 40° C. In addition, although the reaction time of the Diels-Alder reaction naturally varies depending on the substrate used, the reaction time is generally 30 minutes to 30 hours, and preferably 1 hour to 20 hours. Note that the Diels-Alder reaction is preferably performed in an inert gas such as nitrogen or argon.

Next, the hydroxyl group moiety of the alcohol (c) is converted to a leaving group such as a halogen atom, an alkanesulfonyloxy group, or an arenesulfonyloxy group, and thus the compound represented by the general formula (2) is synthesized. The reagent used here for the conversion to the leaving group includes hydrogen chloride, thionyl chloride, sulfuryl chloride, oxalyl chloride, phosphorus trichloride, phosphorus pentachloride, hydrogen bromide, phosphorus tribromide, phosphorus pentabromide, carbon tetrabromide, dimethylbromosulfonium bromide, thionyl bromide, hydrogen iodide, phosphorus triiodide, triphenyl phosphite methiodide, p-toluenesulfonyl chloride, methanesulfonyl chloride, trifluoromethanesulfonyl chloride, trifluoromethanesulfonic anhydride, and the like. The reaction solvent includes, but not particularly limited, ethers such as diethyl ether, tetrahydrofuran, and dioxane; aromatic hydrocarbons such as benzene, toluene, and xylene; halogen-containing hydrocarbon solvents such as dichloromethane and 1,2-dichloroethane; aprotic polar solvents such as N,N-dimethylformamide, acetonitrile, and dimethyl sulfoxide; alcohols such as methanol, ethanol, and 2-propanol; and the like. In particular, dichloromethane, tetrahydrofuran, and toluene are preferable. Note that, for some reaction systems, it is preferable to perform the reaction in the presence of a base in an amount of 1 to 2 equivalents to the reaction substrate. Although the reaction temperature naturally varies depending on the substrate used, the reaction temperature is in a range of generally −30° C. to 200° C., and preferably 10° C. to 100° C. In addition, although the reaction time naturally varies depending on the substrate used, the reaction time is generally 30 minutes to 30 hours, and preferably 1 hour to 20 hours. Note that the reaction is preferably performed in an inert gas such as nitrogen or argon.

The compound represented by the general formula (2) can also be synthesized, for example, according to Scheme 3.

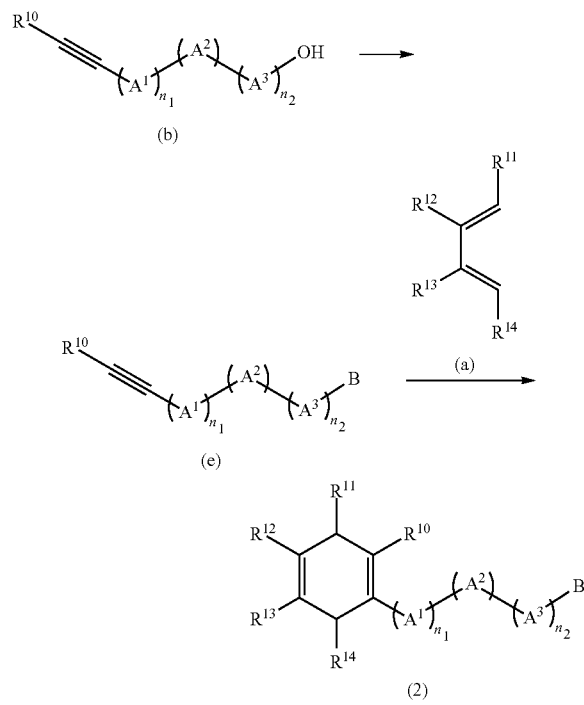

wherein $R^{10}$ to $R^{14}$, $A^1$, $A^2$, $A^3$, $n_1$, $n_2$, and B are the same as described above.

As shown in scheme 3, the hydroxyl group moiety of the alkyne (b) having a substituent is converted to a leaving group such as a halogen atom, an alkanesulfonyloxy group, or an arenesulfonyloxy group. After that, the compound represented by the general formula (2) is synthesized by a Diels-Alder reaction of the compound represented by the general formula (e) with the diene (a) having substituents. A reagent for the conversion to the leaving group, a solvent, and reaction conditions are the same as described in scheme 2 above.

From the compound of the general formula (1), a ruthenium-diamine complex (5) can be produced according to the description in Org. Lett. 9 (2007) p. 4659, for example.

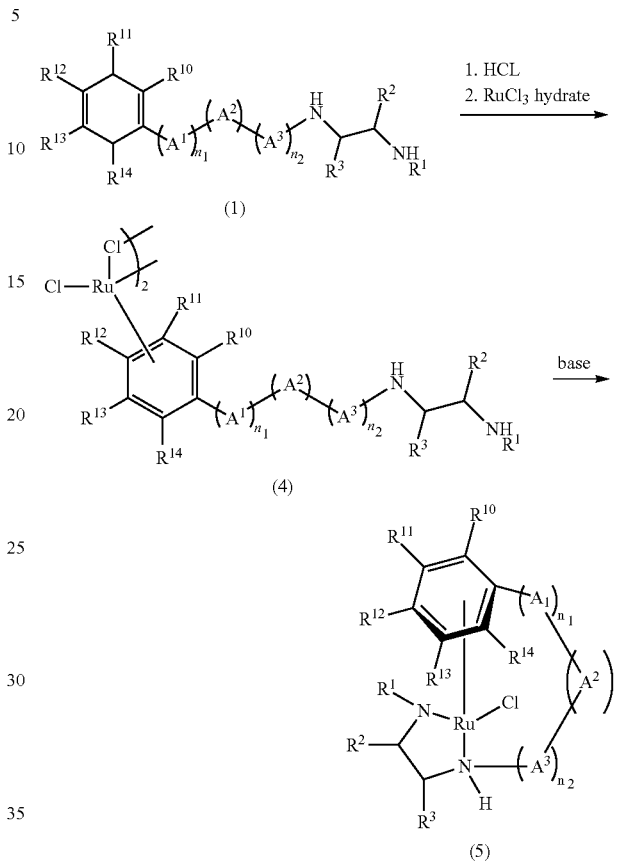

wherein $R^1$ to $R^3$, $R^{10}$ to $R^{14}$, $A^1$, $A^2$, $A^3$, $n_1$, and $n_2$ are the same as described above).

A solvent used for synthesizing a complex of the general formula (4) from the compound of the general formula (1) and ruthenium(III) chloride or hydrate thereof includes, but not particularly limited, aliphatic alcohols such as 2-propanol, n-butanol, 2-butanol, n-pentanol, 2-pentanol, 3-pentanol, 3-methyl-1-butanol, cyclopentanol, 3-methoxy-1-propanol, 2-methoxyethanol, 2-ethoxyethanol, 2-isopropoxyethanol, n-hexanol, 3-methoxy-1-butanol, 3-methoxy-3-methyl-1-butanol, 2-hexanol, 3-hexanol, cyclohexanol, n-heptanol, 2-heptanol, 3-heptanol, cycloheptanol, n-octanol, 2-octanol, 3-octanol, 4-octanol, and cyclooctanol; aromatic alcohols such as phenol, benzyl alcohol, 1-phenylethanol, 2-phenylethanol, o-cresol, m-cresol, p-cresol, 2-methylbenzyl alcohol, 3-methylbenzyl alcohol, and 4-methylbenzyl alcohol; diols such as ethylene glycol, 1,2-propanediol, 1,3-propanediol, 1,2-butanediol, 1,3-butanediol, 1,4-butanediol, ethylene glycol-n-butyl ether, ethylene glycol-iso-butyl ether, and ethylene glycol-n-hexyl ether; derivatives thereof; and the like. One of these solvents may be used alone, or two or more thereof may be used as a mixture. By using two or more solvents in combination, the boiling point of the solvent can be adjusted in a desired range, so that the reaction temperature can be controlled for a reaction under reflux. For example, an alcohol with which a small amount of water is mixed may be used. The amount of the compound of the general formula (1) used is 1 to 20 equivalents, preferably 1 to 10 equivalents, and more preferably 1 to 5 equivalents, to the ruthenium atoms.

The amount of the solvent used is not particularly limited, as long as ruthenium chloride or hydrate thereof can be dissolved therein at the reaction temperature. For example, the amount of the solvent is 2 to 50 times volume (i.e., 2 to 50 mL of the solvent relative to 1 g of ruthenium chloride or hydrate thereof), preferably 2 to 30 times volume, and more preferably 5 to 20 times volume of ruthenium chloride or hydrate thereof. Although the reaction temperature varies depending on the solvent used, the reaction temperature is 60° C. or above, and preferably 100° C. or above, and also 200° C. or below, and preferably 160° C. or below, from the viewpoint of the reaction efficiency.

A solvent used for synthesizing the complex of the general formula (5) from the complex of the general formula (4) includes, but not particularly limited, halogenated solvents such as methylene chloride, dichloroethane, chloroform, and trifluoroethanol; aromatic hydrocarbons such as toluene and xylene; ethers such as diisopropyl ether and tetrahydrofuran; alcohols such as methanol, ethanol, 2-propanol, n-butanol, 2-butanol, and n-pentanol; and the like. Dichloromethane or isopropanol is particularly preferable. One of these solvents may be used alone, or two or more thereof may be used as a mixture. By using two or more solvents in combination, the boiling point of the solvent can be adjusted in a desired range, so that the reaction temperature can be controlled for a reaction under reflux. For example, an alcohol with which a small amount of water is mixed may be used. The base used here includes inorganic bases such as sodium hydroxide, sodium hydrogen carbonate, sodium carbonate, potassium hydroxide, potassium hydrogen carbonate, potassium carbonate, lithium hydroxide, lithium hydrogen carbonate, lithium carbonate, cesium carbonate, magnesium hydroxide, magnesium carbonate, calcium hydroxide, and calcium carbonate; amines such as triethylamine, tripropylamine, tributylamine, pyridine, and triisopropylamine; and the like. Triethylamine is particularly preferable. The amount of the base used is 0.2 to 2 equivalents, and preferably 1 to 1.5 equivalents to the ruthenium atoms. Although the reaction time varies depending on the reaction substrate used, the reaction time is 30 minutes to 20 hours, and preferably 1 hour to 12 hours. This reaction is preferably performed in an inert gas such as nitrogen gas or argon gas.

EXAMPLES

Hereinafter, the present invention will be described in detail based on Examples. However, the present invention is not limited to these Examples.

Note that, in the following Examples and the like, NMR spectra used for identification of complexes and determination of purities thereof were measured with Mercury Plus 300 4N model apparatus manufactured by Varian Technologies Japan Ltd., or Bruker BioSpin Avance III 500 System. For GC analysis, Chirasil-DEX CB (0.25 mm×25 m, 0.25 μm) (manufactured by Varian, Inc.) or HP-1 (0.32 mm×30 m, 0.25 μm) (manufactured by Agilent Technologies, Inc.) was used. For HPLC analysis, YMC-Pack Pro C18 (250×4.6 mm, 5 μm, 12 nm) (manufactured by YMC) was used. Meanwhile, for MS measurement, JMS-T100GCV manufactured by JEOL Ltd. or LCMS-IT-TOF manufactured by Shimadzu Corporation was used.

In addition, the meanings of abbreviations in Examples are as follows.
THF: tetrahydrofuran
Msdpen: N-methanesulfonyl-1,2-diphenylethylenediamine
Tsdpen: N-(p-toluenesulfonyl)-1,2-diphenylethylenediamine
o-TFTs-DPEN: N-(o-trifluoromethylbenzenesulfonyl)-1,2-diphenylethylenediamine
TIPPs-DPEN: N-(2,4,6-triisopropylbenzenesulfonyl)-1,2-diphenylethylenediamine
DIPEA: diisopropylethylamine
MIBK: methyl isobutyl ketone
S/C represents a value represented by the number of moles of the substrate ketone/the number of moles of the catalyst.

Example 1

Production of 4-(4-methylcyclohexa-1,4-dienyl)butan-1-ol and 4-(5-methylcyclohexa-1,4-dienyl)butan-1-ol

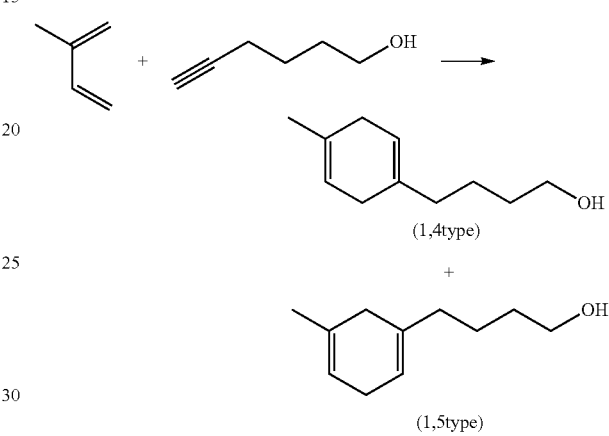

In 45 mL of THF, 1,2-bis(diphenylphosphino)ethane (0.77 g, 1.93 mmol), cobalt bromide (0.41 g, 1.87 mmol), zinc iodide (1.19 g, 3.73 mmol), and zinc (0.24 g, 3.67 mmol) were dissolved, followed by stirring at 70° C. for 15 minutes. After cooling to room temperature, isoprene (7.55 g, 110.83 mmol) was added. Then, 5-hexyn-1-ol (8.94 g, 91.09 mmol) was slowly added dropwise with cooling in a water bath. After stirring at 35° C. for 1 hour, the solvent was evaporated under reduced pressure, and the obtained residue was purified by silica gel column chromatography (hexane/ethyl acetate=3/1). Thus, 13.34 g of the title compounds, alcohols, were obtained as a colorless oily substance. Yield: 88.1% (isomer ratio: 1,4 type/1,5 type=77/23). Note that the following NMR spectrum data are those of the mixture of the two isomers.

$^1$H-NMR (CDCl$_3$, 300 MHz): δ 5.61-5.57 (m, 2H'), 5.43-5.41 (m, 2H), 3.67-3.63 (m, 2H+2H'), 2.58 (brs, 4H), 2.10 (brs, 4H'), 2.08 (t, J=6.9 Hz, 2H'), 2.00 (t, J=7.2 Hz, 2H), 1.76 (s, 3H'), 1.67 (s, 3H), 1.61-1.43 (m, 5H+5H');

HRMS (ESI): calcd for C$_{11}$H$_{19}$O [M+H]+167.1430, found 167.1432

Example 2

Production of 4-(4-methylcyclohexa-1,4-dienyl)butyl 4-methylbenzenesulfonate and 4-(5-methylcyclohexa-1,4-dienyl)butyl 4-methylbenzenesulfonate

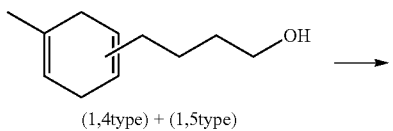

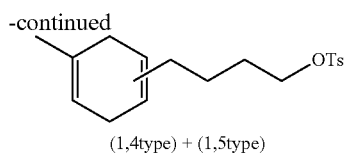

(1,4type) + (1,5type)

The alcohols (12.19 g, 73.32 mmol, isomer ratio: 1,4 type/ 1,5 type=77/23) obtained in Example 1, triethylamine (8.90 g, 87.98 mmol), and 1-methylimidazole (7.22 g, 87.98 mmol) were dissolved in 10 mL of toluene. With cooling in an ice-bath, a toluene solution (40 ml) of p-toluenesulfonyl chloride (15.94 g, 83.58 mmol) was slowly added dropwise, followed by stirring at room temperature for 1 hour. Water was added thereto, and the resultant layers were separated from each other. The obtained organic layer was washed with 2 M hydrochloric acid and water. The solvent was evaporated under reduced pressure, and the obtained residue was purified by silica gel column chromatography (hexane/ethyl acetate=20/1→4/1). Thus, 20.25 g of the title compounds, tosylates, were obtained as a colorless oily substance. Yield: 86.2% (isomer ratio: 1,4 type/1,5 type=77/23). Note that the following NMR spectrum data are those of the mixture of the two isomers.

$^1$H-NMR (CDCl$_3$, 300 MHz): δ 7.80-7.77 (m, 2H+2H'), 7.36-7.33 (m, 2H+2H'), 5.58-5.56 (m, 1H'), 5.51-5.49 (m, 1H'), 5.39-5.38 (m, 1H), 5.35-5.34 (m, 1H), 4.05-4.01 (m, 2H+2H'), 2.53 (brs, 4H), 2.45 (s, 3H+3H'), 2.05 (brs, 4H'), 1.99 (t, J=7.4 Hz, 2H'), 1.91 (t, J=7.4 Hz, 2H), 1.76 (s, 3H'), 1.66 (s, 3H), 1.67-1.58 (m, 2H+2H'), 1.49-1.37 (m, 2H+2H');

HRMS (ESI): calcd for C$_{18}$H$_{24}$O$_3$SNa [M+Na]+343.1338, found 343.1330

Example 3

Production of 4-methyl-N-((1S,2S)-2-(4-(4-methylcyclohexa-1,4-dienyl)butylamino)-1,2-diphenylethyl)benzenesulfonamide and 4-methyl-N-((1S,2S)-2-(4-(5-methylcyclohexa-1,4-dienyl)butylamino)-1,2-diphenylethyl)benzenesulfonamide

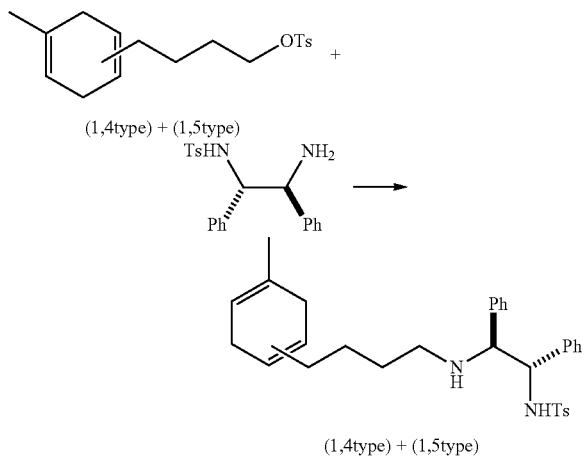

The tosylates (10.45 g, 32.61 mmol, isomer ratio: 1,4 type/ 1,5 type=77/23) obtained in Example 2 were dissolved in 40 ml of toluene, and DIPEA (4.79 g, 32.61 mmol) and (S,S)-TsDPEN (11.95 g, 32.61 mmol) were added thereto, followed by stirring at 135° C. for 14 hours. After that, the solvent was evaporated under reduced pressure, and the obtained residue was purified by silica gel column chromatography (hexane/ ethyl acetate=2/1). Thus, 9.31 g of the title compounds were obtained as a yellow oily substance. Yield: 55.5% (isomer ratio: 1,4 type/1,5 type=77/23). Note that the following NMR spectrum data are those of the mixture of the two isomers.

$^1$H NMR (CDCl$_3$, 300 MHz): δ 7.38-7.36 (m, 2H+2H'), 7.14-7.12 (m, 3H+3H'), 7.05-7.00 (m, 5H+5H'), 6.96-6.88 (m, 4H+4H'), 6.30 (brs, 1H+1H'), 5.60-5.58 (m, 1H'), 5.53-5.51 (m, 1H'), 5.41-5.40 (m, 1H), 5.37-5.36 (m, 1H), 4.24-4.22 (m, 1H+1H'), 3.60-3.58 (m, 1H+1H'), 2.55 (brs, 4H), 2.46-2.37 (m, 1H+1H'), 2.34 (s, 3H+3H'), 2.32-2.23 (m, 1H+1H'), 2.01 (brs, 4H'), 2.01-1.88 (m, 2H+2H'), 1.77 (s, 3H'), 1.67 (s, 3H), 1.46-1.28 (m, 5H+5H');

HRMS (ESI): calcd for C$_{32}$H$_{39}$N$_2$O$_2$S[M+H]+515.2727, found 515.2747

Example 4

Production of 4-methyl-N-((1S,2S)-2-(4-(4-methylcyclohexa-1,4-dienyl)butylamino)-1,2-diphenylethyl)benzenesulfonamide hydrochloride and 4-methyl-N-((1S,2S)-2-(4-(5-methylcyclohexa-1,4-dienyl)butylamino)-1,2-diphenylethyl)benzenesulfonamide hydrochloride

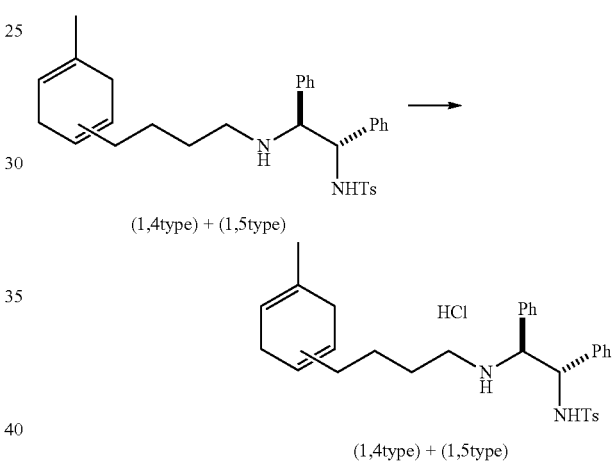

The amides (8.55 g, 16.61 mmol, isomer ratio: 1, 4 type/1,5 type=77/23) obtained in Example 3 were dissolved in 33 ml of toluene. Under ice-cooling, a 1N HCl (methanolic solution) (3.46 g, 33.22 mmol) was added, followed by stirring at room temperature for 20 minutes. After that, the solvent was evaporated under reduced pressure. Thus, 8.85 g of the title compounds, diamine hydrochlorides, were obtained as a white solid. Yield: 96.7% (isomer ratio: 1,4 type/1,5 type=77/ 23).

$^1$H-NMR (d$_6$-DMSO, 300 MHz) δ: 9.61 (brs, 1H+1H'), 9.15 (brs, 1H+1H'), 8.85 (d, 1H+1H'), 7.29-6.79 (m, 14H+ 14H'), 5.55 (m, 1H'), 5.48 (m, 1H'), 5.36 (m, 1H), 5.31 (m, 1H), 4.82 (m, 1H+1H'), 4.54 (m, 1H+1H'), 2.66 (brs, 4H), 2.20 (s, 3H+3H'), 1.99 (brs, 4H'), 1.98-1.90 (m, 2H'), 1.90-1.82 (m, 2H), 1.71 (s, 3H'), 1.70-1.52 (m, 2H+2H'), 1.61 (s, 3H), 1.38-1.18 (m, 2H+2H');

HRMS (ESI): calcd for C$_{32}$H$_{39}$N$_2$O$_2$S [M−Cl]+515.2727, found 515.2728

Example 5

Production of N-[(1S,2S)-1,2-diphenyl-2-(4-(4-methylphenyl)butylamino)ethyl]-4-methylbenzenesulfonamide ammonium chloride ruthenium dimer and N-[(1S,2S)-1,2-diphenyl-2-(4-(3-methylphenyl)butylamino)ethyl]-4-methylbenzenesulfonamide ammonium chloride ruthenium dimer

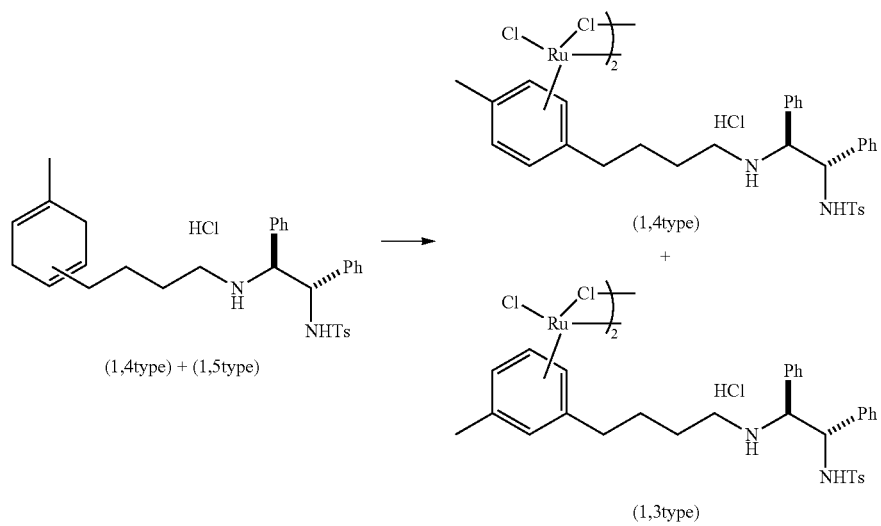

The hydrochlorides (7.42 g, 13.46 mmol, isomer ratio: 1,4 type/1,5 type=77/23) obtained in Example 4 and ruthenium trichloride.trihydrate (3.20 g, 12.25 mmol) were dissolved in a mixture solvent of 110 ml of 3-methoxypropanol and 37 ml of water, followed by stirring at 120° C. for 1 hour. The solvent was evaporated under reduced pressure, and diethyl ether was added to the obtained residue, followed by stirring at room temperature for 15 minutes. The precipitated crystals were filtered. Thus, 10.15 g of the title compounds, ruthenium dimers, were obtained. Yield: 52.3%. The following NMR spectrum data are those of the major product (1,4 type).

$^1$H NMR (d$_6$-DMSO, 500 MHz): δ 9.61 (brs, 2H), 9.11 (brs, 2H), 8.78 (d, J=9.1 Hz, 2H), 7.30-6.88 (m, 28H), 6.82-6.81 (m, 8H), 4.83 (m, 2H), 4.56 (m, 2H), 2.71 (brs, 4H), 2.35 (t, J=7.5 Hz, 4H), 2.22 (s, 6H), 2.10 (s, 6H), 1.80-1.60 (m, 4H), 1.60-1.42 (m, 4H);

HRMS (FD): calcd for $C_{32}H_{35}ClN_2O_2RuS$ [M/2−2HCl]+. 648.1156, found 648.1182

Example 6

Production of N-[(1S,2S)-1,2-diphenyl-2-(4-(4-methylphenyl)butylamino)ethyl]-4-methylbenzenesulfonamide ammonium chloride ruthenium monomer and N-[(1S,2S)-1,2-diphenyl-2-(4-(3-methylphenyl)butylamino)ethyl]-4-methylbenzenesulfonamide ammonium chloride ruthenium monomer

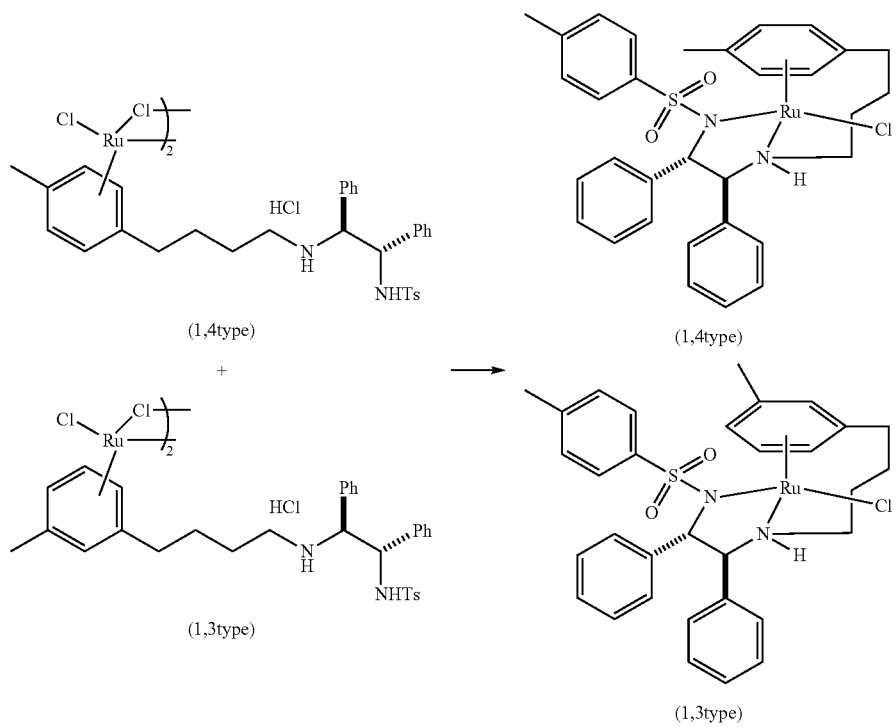

The ruthenium dimers (9.12 g, 6.32 mmol) obtained in Example 5 were dissolved in 155 ml of 2-propanol, and triethylamine (2.53 g, 25.29 mmol) was added thereto, followed by stirring at 60° C. for 1 hour. After that, the solvent was evaporated under reduced pressure, and the obtained residue was purified by silica gel chromatography (chloroform/methanol=20/1). Thus, 6.77 g of the title compounds, ruthenium monomers, were obtained. Yield: 82.6% (the chemical purity based on HPLC was 97.2%). The following NMR spectrum data are those of the major product (1,4 type).

$^1$H NMR (CD$_2$Cl$_2$, 500 MHz): δ 7.17 (d, J=7.9 Hz, 2H), 7.10-7.05 (m, 3H), 6.86 (d, J=7.9 Hz, 2H), 6.82-6.79 (m, 1H), 6.74 (d, J=6.4 Hz, 2H), 6.68 (dd, J=7.9 Hz, 2H), 6.56 (d, J=7.9 Hz, 2H), 6.18 (d, J=5.6 Hz, 1H), 5.55 (d, J=6.3 Hz, 1H), 5.35 (d, J=6.3 Hz, 1H), 5.29 (d, J=5.6 Hz, 1H), 4.73-4.70 (m, 1H), 3.97 (d, J=11.0 Hz, 1H), 3.81 (dd, J=11.0, 12.2 Hz, 1H), 3.52-3.47 (m, 1H), 3.13-3.07 (m, 1H), 2.85-2.81 (m, 1H), 2.75-2.69 (m, 1H), 2.44 (s, 3H), 2.26 (s, 3H), 2.28-2.17 (m, 1H), 2.15-2.04 (m, 1H), 1.96-1.88 (m, 1H), 1.67-1.60 (m, 1H);

HRMS (ESI): calcd for C$_{32}$H$_{36}$ClN$_2$O$_2$RuS [M+H]+ 649.1224, found 649.1224

Example 7

Production of N-((1S,2S)-2-(4-(4-methylcyclohexa-1,4-dienyl)butylamino)-1,2-diphenylethyl)methanesulfonamide and N-((1S,2S)-2-(4-(5-methylcyclohexa-1,4-dienyl)butylamino)-1,2-diphenylethyl)methanesulfonamide

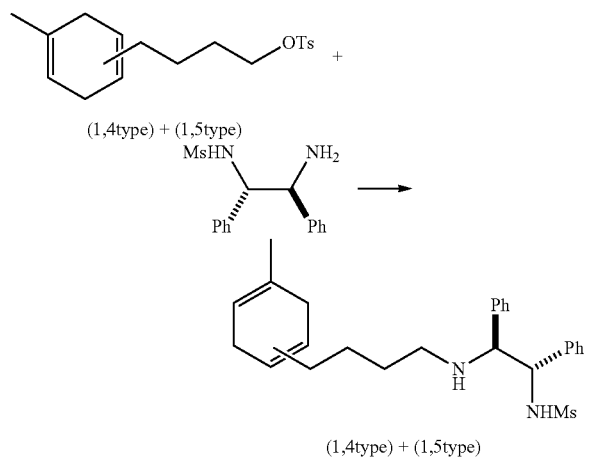

The tosylates (5.11 g, 15.95 mmol) obtained in Example 2 were dissolved in 20 ml of toluene, and DIPEA (2.05 g, 15.95 mmol) and (S,S)-MsDPEN (4.63 g, 15.95 mmol) were added thereto, followed by stirring at 135° C. for 16 hours. After that, the solvent was evaporated under reduced pressure, and the obtained residue was purified by silica gel column chromatography (hexane/ethyl acetate=2/1). Thus, 5.72 g of the title compounds, diamines, were obtained as a yellow oily substance.

Yield: 81.8% (isomer ratio: 1,4 type/1,5 type=77/23). Note that the following NMR spectrum data are those of the mixture of the two isomers.

$^1$H NMR (CDCl$_3$, 300 MHz): δ 7.26-7.19 (m, 10H+10H'), 6.23 (brs, 1H+1H'), 5.59-5.58 (m, 1H'), 5.52-5.51 (m, 1H'), 5.40 (m, 1H), 5.36 (m, 1H), 4.47-4.44 (m, 1H+1H'), 3.75-3.72 (m, 1H+1H'), 2.55 (brs, 4H), 2.46-2.37 (m, 1H+1H'), 2.34 (s, 3H+3H'), 2.32-2.23 (m, 1H+1H'), 2.01 (brs, 4H'), 2.01-1.88 (m, 2H+2H'), 1.77 (s, 3H'), 1.67 (s, 3H), 1.46-1.28 (m, 5H+5H');

HRMS (ESI): calcd for C$_{26}$H$_{35}$N$_2$O$_2$S [M+H]+439.2414, found 439.2409

Example 8

Production of N-((1S,2S)-2-(4-(4-methylcyclohexa-1,4-dienyl)butylamino)-1,2-diphenylethyl)methanesulfonamide hydrochloride and N-((1S,2S)-2-(4-(5-methylcyclohexa-1,4-dienyl)butylamino)-1,2-diphenylethyl)methanesulfonamide hydrochloride

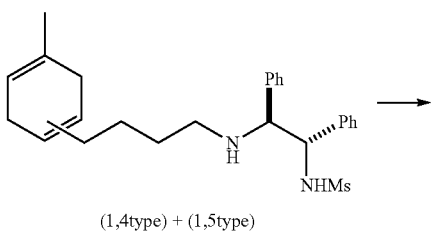

The diamines (5.11 g, 11.65 mmol) obtained in Example 7 were dissolved in 20 ml of toluene. Under ice-cooling, a 1N HCl (methanolic solution) (2.43 g, 23.30 mmol) was added thereto, followed by stirring at room temperature for 20 minutes. After that, the solvent was evaporated under reduced pressure. Thus, 5.14 g of the title compounds, diamine hydrochlorides, were obtained as a white solid. Yield: 92.9% (isomer ratio: 1,4 type/1,5 type=77/23). Note that the following NMR spectrum data are those of the mixture of the two isomers.

$^1$H-NMR (d$_6$-DMSO, 300 MHz) δ: 9.94 (brs, 1H+1H'), 9.08 (brs, 1H+1H'), 8.34 (d, 1H+1H'), 7.39-7.00 (m, 10H+10H'), 5.54 (m, 1H'), 5.47 (m, 1H'), 5.35 (m, 1H), 5.30 (m, 1H), 4.90 (m, 1H+1H'), 4.56 (m, 1H+1H'), 2.72-2.56 (m, 6H+2H'), 2.47 (s, 3H+3H'), 1.98 (brs, 4H'), 1.93 (t, J=6.9 Hz, 2H'), 1.85 (t, J=7.2 Hz, 2H), 1.71 (s, 3H'), 1.70-1.52 (m, 2H+2H'), 1.61 (s, 3H), 1.38-1.18 (m, 2H+2H');

HRMS (ESI): calcd for C$_{26}$H$_{35}$N$_2$O$_2$S [M−Cl]+439.2414, found 439.2422

Example 9

Production of N-[(1S,2S)-1,2-diphenyl-2-(4-(4-methylphenyl)butylamino)-ethyl]-methanesulfonamide ammonium chloride ruthenium dimer and N-[(1S,2S)-1,2-diphenyl-2-(4-(3-methylphenyl)butylamino)-ethyl]-methanesulfonamide ammonium chloride ruthenium dimer

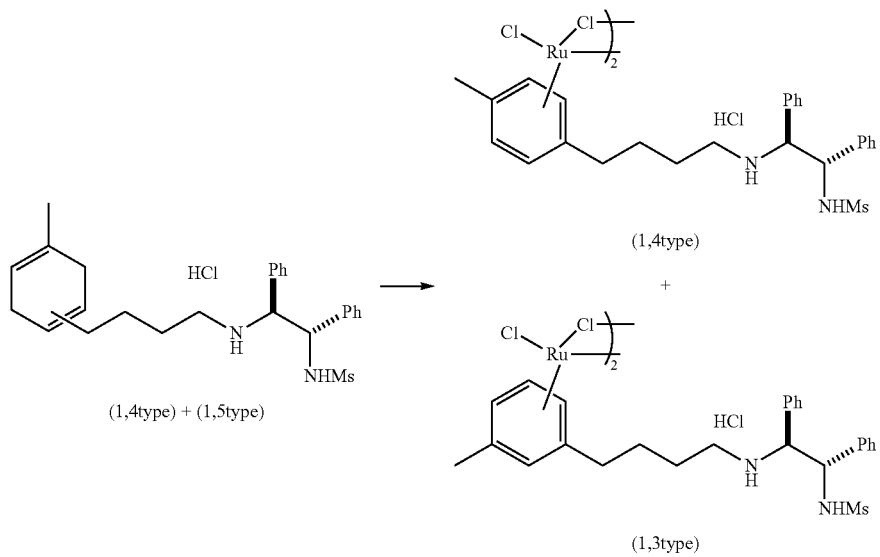

The diamine hydrochlorides (4.05 g, 8.52 mmol) obtained in Example 8 and ruthenium trichloride.trihydrate (2.03 g, 7.76 mmol) were dissolved in a mixture solvent of 60 ml of 3-methoxypropanol and 19 ml of water, followed by stirring at 120° C. for 1 hour. The solvent was evaporated under reduced pressure, and diethyl ether was added to the obtained residue, followed by stirring at room temperature for 15 minutes. The precipitated crystals were filtered. Thus, 5.49 g of the title compounds, ruthenium dimers, were obtained. Yield: 49.9%. The following NMR spectrum data are those of the major product (1,4 type).

$^1$H NMR (d$_6$-DMSO, 500 MHz): δ 9.87 (brs, 2H), 9.04 (brs, 2H), 8.27 (d, J=9.4 Hz, 2H), 7.39-7.01 (m, 20H), 5.76-5.73 (m, 8H), 4.91 (m, 2H), 4.59 (m, 2H), 2.70 (brs, 4H), 2.62 (s, 6H), 2.35 (t, J=7.7 Hz, 4H), 2.09 (s, 6H), 1.80-1.60 (m, 4H), 1.60-1.41 (m, 4H);

HRMS (FD): calcd for $C_{26}H_{31}ClN_2O_2RuS$ [M/2−2HCl]+ .572.0841, found 572.0863

Example 10

Production of N-[(1S,2S)-1,2-diphenyl-2-(4-(4-methylphenyl)butylamino)ethyl]-methanesulfonamide ammonium chloride ruthenium monomer and N-[(1S,2S)-1,2-diphenyl-2-(4-(3-methylphenyl)butylamino)ethyl]-methanesulfonamide ammonium chloride ruthenium monomer

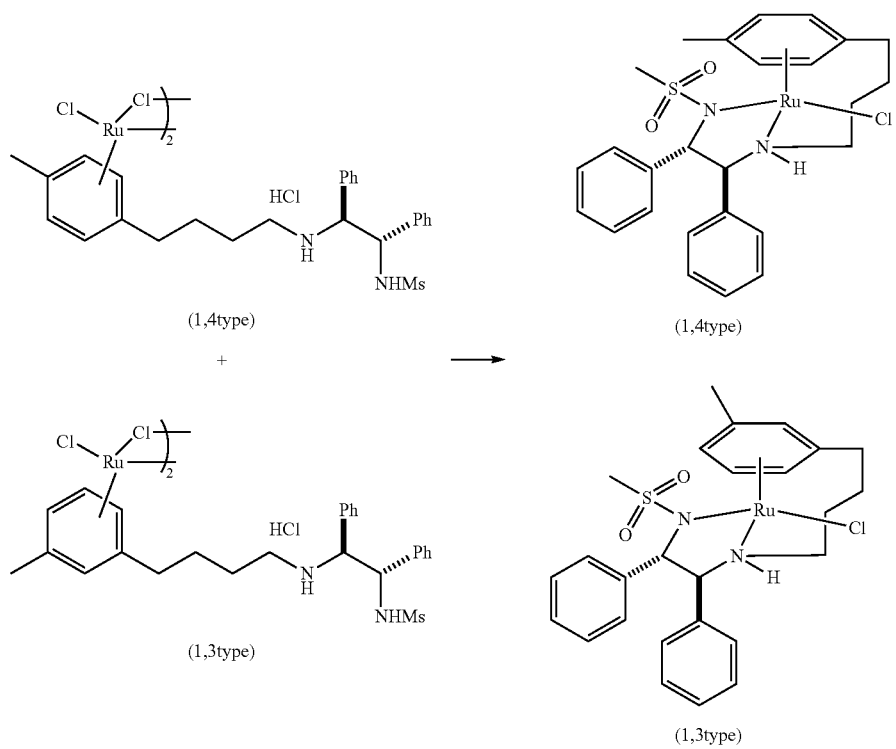

The ruthenium dimers (4.49 g, 3.48 mmol) of Example 9 were dissolved in 85 ml of 2-propanol, and triethylamine (1.45 g, 13.92 mmol) was added thereto, followed by stirring at 60° C. for 1 hour. After that, the solvent was evaporated under reduced pressure, and the obtained residue was purified by silica gel chromatography (chloroform/methanol=20/1). Thus, 3.38 g of the title compounds, ruthenium monomers, were obtained.

Yield: 69.3% (the chemical purity based on HPLC was 98.2%). The following NMR spectrum data are those of the major product (1,4 type).

$^1$H NMR (CD$_2$Cl$_2$, 500 MHz): δ 7.17-7.13 (m, 3H), 7.10-7.07 (m, 3H) 6.97-6.95 (m, 2H), 6.85-6.83 (m, 2H), 5.84 (d, J=5.5 Hz, 1H), 5.51 (d, J=6.1 Hz, 1H), 5.46 (d, J=6.1 Hz, 1H), 5.38 (d, J=5.5 Hz, 1H), 4.41 (m, 1H), 4.01 (d, J=10.7 Hz, 1H), 3.86 (dd, J=10.7, 12.2 Hz, 1H), 3.43-3.38 (m, 1H), 3.12-3.07 (m, 1H), 2.80-2.71 (m, 2H), 2.47 (s, 3H), 2.37 (s, 3H), 2.25-2.17 (m, 1H), 2.11-2.02 (m, 1H), 1.98-1.90 (m, 1H), 1.77-1.68 (m, 1H);

HRMS (ESI): calcd for C$_{26}$H$_{32}$ClN$_2$O$_2$RuS [M+H]+ 573.0911, found 573.0912

Example 11

Production of 4-(4,5-dimethylcyclohexa-1,4-dienyl)butan-1-ol

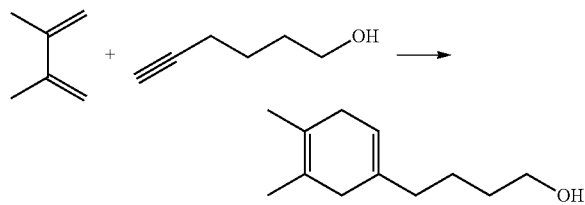

In 40 mL of THF, 1,2-bis(diphenylphosphino)ethane (800 mg, 2.00 mmol), cobalt bromide (437 mg, 2.00 mmol), zinc iodide (1.28 g, 4.00 mmol), and zinc (260 mg, 4.00 mmol) were dissolved, followed by stirring at 70° C. for 15 minutes. After cooling to room temperature, 2,3-dimethyl-1,3-butadiene (9.86 g, 120 mmol) was added. Then, 5-hexyn-1-ol (9.8 g, 100 mmol) was slowly added dropwise with cooling in a water bath. After stirring at 35° C. for 1 hour, the solvent was evaporated under reduced pressure, and the obtained residue was purified by silica gel column chromatography (hexane/ethyl acetate=3/1). Thus, 11.5 g of the title compound, an alcohol, was obtained as a colorless oily substance. Yield: 63.4%.

$^1$H NMR (CDCl$_3$, 300 MHz): δ 5.56-5.41 (m, 1H), 3.67-3.63 (m, 2H), 2.61-2.48 (m, 2H), 2.11-1.98 (m, 3H), 1.63 (s, 6H), 1.79-1.46 (m, 4H), 1.28 (brs, 1H)

Example 12

Production of 4-(4,5-dimethylcyclohexa-1,4-dienyl)butyl 4-methylbenzenesulfonate

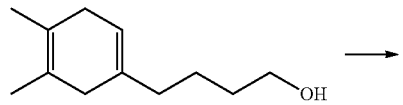

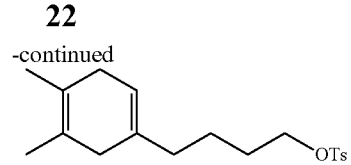

In 55 mL of toluene, 4-(4,5-dimethylcyclo-1,4-diene)butan-1-ol (11.0 g, 61.0 mmol), triethylamine (7.40 g, 73.08 mmol), and 1-methylimidazole (6.0 g, 73.0 mmol) were dissolved. With cooling in an ice-bath, a toluene solution (40 ml) of p-toluenesulfonyl chloride (13.9 g, 73.1 mmol) was slowly added dropwise, followed by stirring at room temperature for 1 hour. Water was added thereto, and the resultant layers were separated from each other. The obtained organic layer was washed with 2 M hydrochloric acid and water. The solvent was evaporated under reduced pressure, and the obtained residue was purified by silica gel column chromatography (hexane/ethyl acetate=20/1→4/1). Thus, 16.3 g of the title compound, a tosylate, was obtained. Yield: 80%.

$^1$H NMR (CDCl$_3$, 300 MHz): δ 7.80-7.77 (d, 2H), 7.36-7.33 (d, 2H), 5.40-5.28 (m, 1H), 4.05-4.00 (m, 2H), 2.53 (brs, 2H), 2.45 (s, 3H), 2.05-1.89 (m, 3H), 1.79-1.74 (m, 3H), 1.67 (s, 6H), 1.60-1.41 (m, 2H)

Example 13

Production of 4-methyl-N-((1S,2S)-2-(4-(4,5-dimethylcyclohexa-1,4-dienyl)butylamino)-1,2-diphenylethyl)benzenesulfonamide hydrochloride

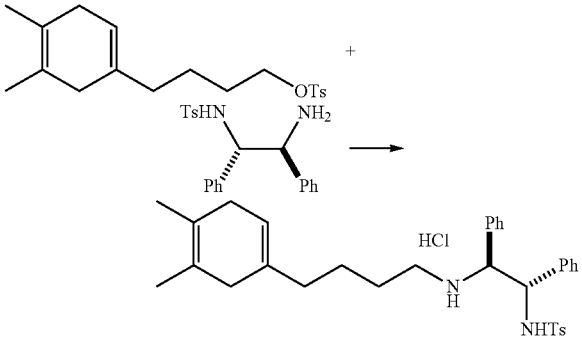

In 30 ml of toluene, 4-(4,5-dimethylcyclo-1,4-diene)butyl-p-toluenesulfonate (3.3 g, 9.87 mmol) was dissolved, and DIPEA (1.40 g, 10.79 mmol) and (S,S)-TsDPEN (3.3 g, 90.0 mmol) were added thereto, followed by stirring at 130° C. for 14 hours. After that, the solvent was evaporated under reduced pressure, and the obtained residue was purified by silica gel column chromatography (hexane/ethyl acetate=2/1). Then, a 1 M methanolic hydrochloric acid solution was added under ice-cooling, followed by stirring at room temperature for 20 minutes. After that, the solvent was evaporated under reduced pressure. Thus, 2.47 g of the title compound, a diamine hydrochloride, was obtained as a white solid. Yield: 44.3%.

$^1$H NMR (DMSO-d$_6$, 300 MHz): δ 9.80 (brs, 1H), 9.22 (brs, 1H), 9.01 (brs, 1H), 7.29-7.21 (m, 7H), 6.99-6.82 (m, 7H), 5.40-5.28 (m, 1H), 4.90-4.84 (m, 1H), 2.63 (brs, 2H), 2.40 (brs, 2H), 2.21 (s, 3H), 1.99-1.89 (m, 2H), 1.75-1.62 (m, 2H), 1.58 (s, 6H), 1.60-1.41 (m, 2H)

HRMS (ESI): calcd for C$_{33}$H$_{41}$N$_2$O$_2$S [M−Cl]+529.2892, found 529.2892

Example 14

Production of N-[(1S,2S)-1,2-diphenyl-2-(4-(3,4-dimethylphenyl)butylamino)-ethyl]-4-methylbenzenesulfonamide ammonium chloride ruthenium dimer

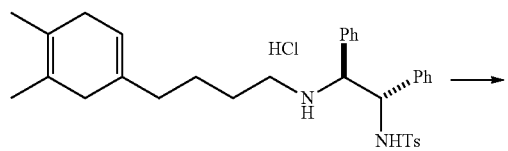

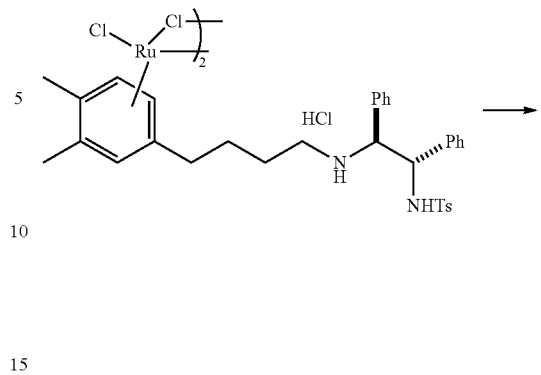

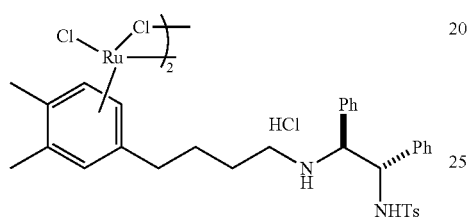

In a mixture solvent of 35 ml of 2-methoxyethanol and 3.7 ml of water, 4-methyl-N-((1S,2S)-2-(4-(4,5-dimethylcyclohexa-1,4-dienyl)butylamino)-1,2-diphenylethyl)benzenesulfonamide hydrochloride (1.0 g, 1.77 mmol) and ruthenium trichloride.trihydrate (3.86 mg, 1.45 mmol) were dissolved, followed by stirring at 120° C. for 1 hour. The solvent was evaporated under reduced pressure, and diethyl ether was added to the obtained residue, followed by stirring at room temperature for 15 minutes. The precipitated crystals were filtered. Thus, 1.39 g of the title compound, a ruthenium dimer, was obtained. Yield: 82.5%.

$^1$H NMR (DMSO-d6, 300 MHz): δ 9.80 (brs, 1H), 9.22 (brs, 1H), 8.91 (brs, 1H), 7.28-7.19 (m, 7H), 6.98 (d, J=8 Hz, 2H), 6.99-6.82 (m, 7H), 5.40-5.28 (m, 1H), 4.90-4.84 (m, 1H), 2.63 (brs, 2H), 2.40 (brs, 2H), 2.21 (s, 3H), 1.99-1.89 (m, 2H), 1.75-1.62 (m, 2H), 1.58 (s, 6H), 1.60-1.41 (m, 2H)

Example 15

Production of N-[(1S,2S)-1,2-diphenyl-2-(4-(3,4-dimethylphenyl)butylamino) ethyl]-4-methylbenzenesulfonamide ammonium chloride ruthenium monomer The ruthenium dimer (870 mg, 1.27 mmol) obtained in Example 14 was dissolved in 60 ml of 2-propanol, and triethylamine (514 mg, 5.07 mmol) was added thereto, followed by stirring at 60° C. for 1 hour. After that, the solvent was evaporated under reduced pressure, and the obtained residue was purified by silica gel chromatography (chloroform/methanol=20/1). Thus, 500 mg of the title compound, a ruthenium monomer, was obtained. Yield: 42.7%.

HRMS (ESI): calcd for $C_{33}H_{38}ClN_2O_2RuS$ [M+H]+ 663.1381, found 663.1371

Example 16

Production of 2-((4-methylcyclohexa-1,4-dienyl)methoxy)ethanol and 2-((5-methylcyclohexa-1,4-dienyl)methoxy)ethanol

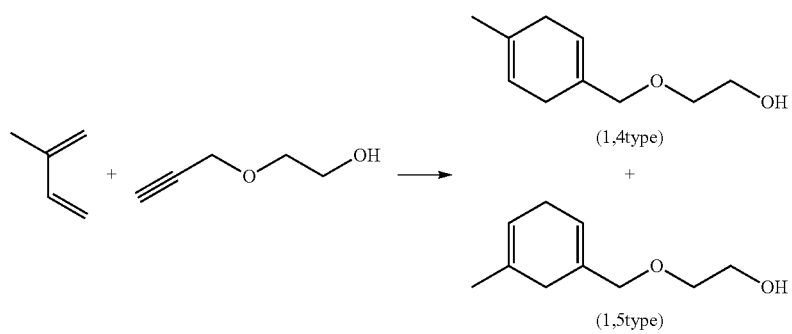

In 460 ml of THF, 1,2-bis(diphenylphosphino)ethane (7.74 g, 0.019 mol), cobalt bromide (4.05 g, 0.019 mol), zinc iodide (11.82 g, 0.037 mol), and zinc (2.42 g, 0.037 mol) were dissolved, followed by stirring at 70° C. for 15 minutes. After cooling to room temperature, isoprene (74.89 g, 1.10 mol) was added. Then, an alkyne alcohol (92.70 g, 0.93 mol) was slowly added dropwise with cooling in a water bath. After stirring at 35° C. for 1 hour, the solvent was evaporated under reduced pressure, and the obtained crude product was purified by Claisen distillation (101 to 113° C./3 torr). Thus, 106.6 g of the title compounds, diene alcohols, were obtained as a colorless oily substance.

Yield: 68.5% (1, 4 type/1, 5 type=91/9). Note that the following NMR spectrum data are those of the major product (1,4 type).

$^1$H NMR (CDCl$_3$, 300 MHz): δ 5.71-5.70 (m, 1H), 5.45-5.43 (m, 1H), 3.93 (s, 2H), 3.75-3.70 (m, 2H), 3.52-3.48 (m, 2H), 2.64 (brs, 4H), 2.31 (brs, 1H), 1.68 (s, 3H);

HRMS (ESI): calcd for C$_{10}$H$_{17}$O [M+H]+167.1430, found 167.1432

Example 17

Production of 2-((4-methylcyclohexa-1,4-dienyl)methoxy)ethyl 4-methylbenzenesulfonate and 2-((5-methylcyclohexa-1,4-dienyl)methoxy)ethyl 4-methylbenzenesulfonate

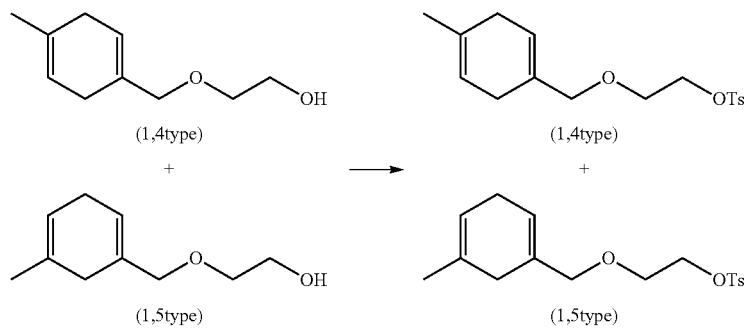 [SMILES: CC1=CCC(COCCO)=CC1 ; CC1=CCC(COCCOS(=O)(=O)c2ccc(C)cc2)=CC1 ; CC1=CCC=C(COCCO)C1 ; CC1=CCC=C(COCCOS(=O)(=O)c2ccc(C)cc2)C1]

The diene alcohols (100.00 g, 0.59 mol) obtained in Example 16, triethylamine (90.29 g, 0.89 mol), and 1-methylimidazole (73.20 g, 0.89 mol) were dissolved in 400 ml of toluene. With cooling in an ice-bath, a toluene solution (400 ml) of p-toluenesulfonyl chloride (130.33 g, 0.68 mol) was slowly added dropwise, followed by stirring at room temperature for 1 hour. Water was added thereto, and the resultant layers were separated from each other. The obtained organic layer was washed with 15% sulfuric acid, water, and saturated aqueous sodium hydrogen carbonate in this order. The solvent was evaporated under reduced pressure. Thus, 188.01 g of the target title compounds, tosylates, were obtained as a colorless oily substance. Yield: 98.1%. Note that the following NMR spectrum data are those of the major product (1,4 type).

$^1$H NMR (CDCl$_3$, 300 MHz): δ 7.80 (d, J=8.3 Hz, 2H), 7.33 (d, J=8.3 Hz, 2H), 5.64-5.63 (m, 1H), 5.41-5.40 (m, 1H), 4.18-4.14 (m, 2H), 3.84 (s, 2H), 3.58-3.55 (m, 2H), 2.58 (brs, 4H), 2.44 (s, 3H), 1.67 (s, 3H);

HRMS (ESI): calcd for C$_{17}$H$_{23}$O$_4$S [M+H]+323.1312, found 323.1325

Example 18

Production of 4-methyl-N-((1R,2R)-2-(2-((4-methylcyclohexa-1,4-dienyl)methoxy)ethylamino)-1,2-diphenylethyl)benzenesulfonamide hydrochloride and 4-methyl-N-((1R,2R)-2-(2-((5-methylcyclohexa-1,4-dienyl)methoxy)ethylamino)-1,2-diphenylethyl)benzenesulfonamide hydrochloride

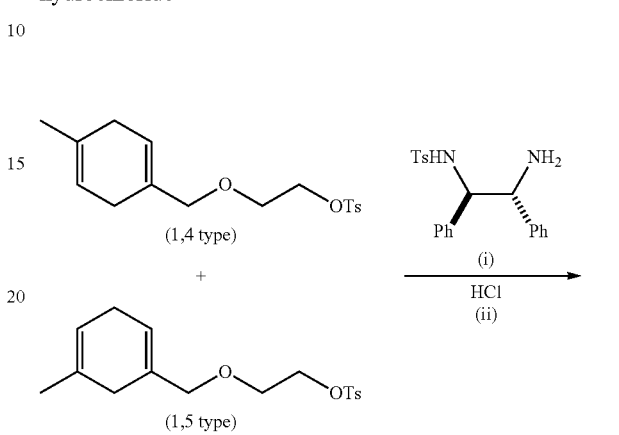

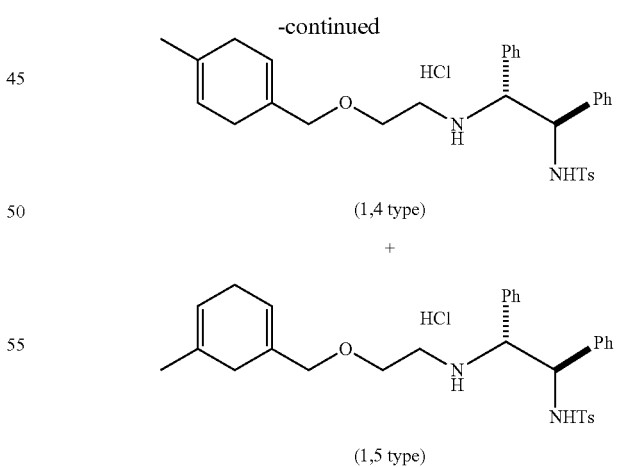

The tosylates (2.2 g, 6.9 mmol) obtained in Example 17 were dissolved in 10 ml of toluene, and DIPEA (0.90 g, 6.9 mmol) and (R,R)-TsDPEN (2.53 g, 6.9 mmol) were added thereto, followed by stirring at 135° C. for 27 hours. Water was added thereto, and the resultant layers were separated from each other. The obtained organic layer was washed with water, and then 20% hydrochloric acid was added thereto. After stirring at room temperature for 1 hour, the precipitated crystals were collected by filtration under ice-cooling. Thus, 3.14 g of the target title compounds, diamine hydrochlorides, were obtained as a white solid. Yield: 82.3%. Note that the following NMR spectrum data are those of the major product (1,4 type).

H-NMR (d$_6$-DMSO, 300 MHz) δ: 9.76 (brs, 1H), 8.98-8.80 (m, 2H), 7.30-6.72 (m, 14H), 5.68 (m, 1H), 5.42 (m, 1H), 4.84 (m, 1H), 4.62 (m, 1H), 3.85 (s, 2H), 3.61 (m, 2H), 3.06-2.80 (m, 2H), 2.57 (brs, 4H), 2.21 (s, 3H), 1.64 (s, 3H);

HRMS (ESI): calcd for C$_{31}$H$_{37}$N$_2$O$_3$S [M−Cl]+517.2519, found 517.2523

Example 19

Production of N-[(1R,2R)-1,2-diphenyl-2-(2-(4-methylbenzyloxy)ethylamino)-ethyl]-4-methylbenzenesulfonamide ammonium chloride ruthenium monomer and N-[(1R,2R)-1,2-diphenyl-2-(2-(3-methylbenzyloxy)ethylamino)-ethyl]-4-methylbenzenesulfonamide ammonium chloride ruthenium monomer

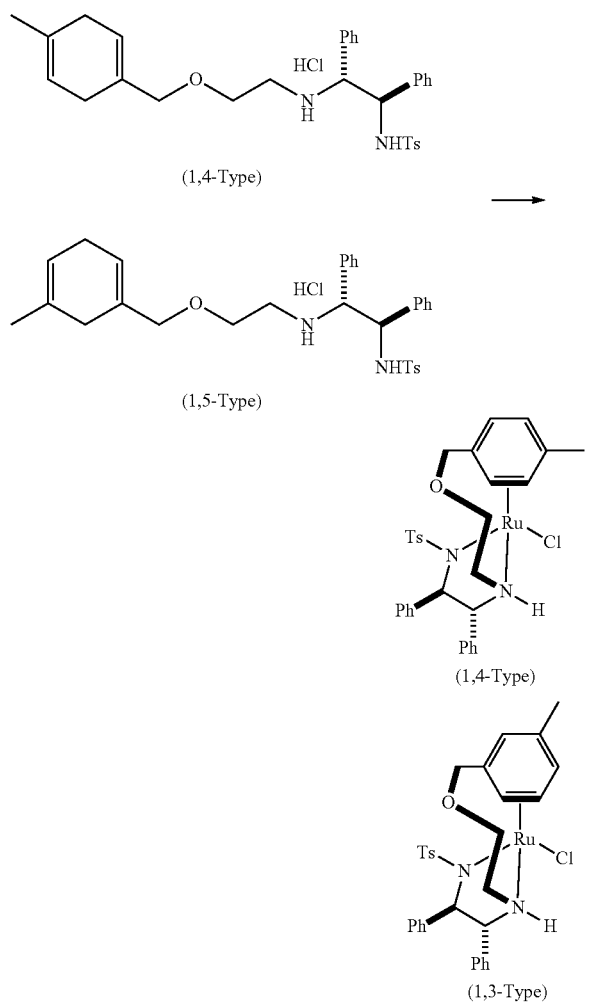

The diamine hydrochlorides (25.15 g, 45.20 mmol) of Example 18 were dissolved in a mixture solvent of 375 ml of 3-methoxypropanol and 75 ml of water. Ruthenium trichloride.trihydrate (10.74 g, 41.09 mmol) and sodium hydrogen carbonate (3.45 g, 41.09 mmol) were added thereto, followed by stirring at 120° C. for 45 minutes. After 3-methoxypropanol was recovered, 425 ml of MIBK and triethylamine (16.63 g, 164.4 mmol) were added, followed by stirring at 60° C. for 1 hour. After washing with 0.3 M hydrochloric acid, crystallization was performed by adding heptane. The precipitated crystals were collected by filtration. Thus, 22.26 g of the title compounds, ruthenium monomers, were obtained. Yield: 83.3%. Note that the following NMR spectrum data are those of the major product (1,4 type).

$^1$H NMR (CD$_2$Cl$_2$, 500 MHz): δ 7.21 (d, J=8.0 Hz, 2H), 7.17-7.08 (m, 4H), 6.88 (d, J=8.0 Hz, 2H), 6.84 (d, J=7.3 Hz, 1H), 6.75-6.69 (m, 4H), 6.60 (d, J=7.3 Hz, 2H), 6.05 (brd, J=3.6 Hz, 1H), 5.75 (d, J=6.3 Hz, 1H), 5.62 (d, J=6.3 Hz, 1H), 5.46 (brd, J=3.6 Hz, 1H), 4.96-4.92 (m, 1H), 4.58-4.45 (m, 2H), 3.98-3.91 (m, 4H), 3.60-3.56 (m, 1H), 3.14-3.10 (m, 1H), 2.52 (s, 3H), 2.26 (s, 3H);

HRMS (ESI): calcd for C$_{31}$H$_{34}$ClN$_2$O$_3$RuS [M+H]+ 651.1017, found 651.1008

Example 20

Production of N-((1R,2R)-2-(2-((4-methylcyclohexa-1,4-dienyl)methoxy)ethylamino)-1,2-diphenylethyl)-2-(trifluoromethyl)benzenesulfon amide hydrochloride

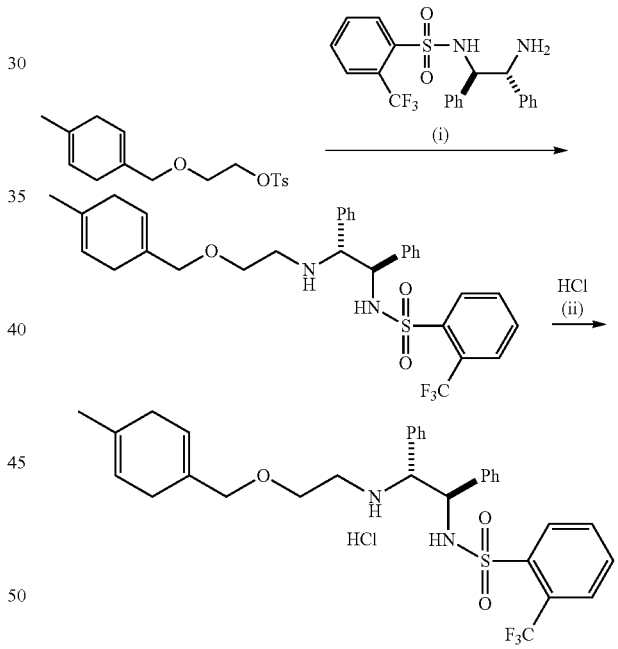

In 31.6 ml of toluene, 8.07 g (26.1 mmol) of the tosylate obtained in Example 17 was dissolved, and 3.38 g (26.2 mmol) of DIPEA, 10.00 g (23.8 mmol) of (R,R)-o-TFTsD-PEN, and 4.34 g (26.2 mmol) of potassium iodide were added thereto, followed by stirring at 135° C. for 6 hours. Then, the reaction liquid was concentrated, and purified by silica gel column chromatography. Thus, 10.1 g of a diamine was obtained. Yield: 74.5%. After that, 110 ml of dichloromethane and 65.3 ml of a 1N HCl (methanolic solution) were added to 10.1 g (17.7 mmol) of the diamine, followed by stirring for 0.5 hours. Then, the solvent was removed. Thus, 11.1 g of the target diamine hydrochloride was obtained. Yield: 93.9%.

H-NMR (d$_6$-DMSO, 300 MHz) δ: 1.62 (m, 3H), 2.60 (s, 3H), 2.78-3.12 (m, 2H), 3.52-3.70 (m, 2H), 3.86 (s, 2H), 4.75

(m, 1H), 4.92 (m, 1H), 5.40 (m, 1H), 5.68 (m, 1H), 6.75-7.35 (m, 10H), 7.40 (t, 1H), 7.50 (t, 1H), 7.60 (d, 1H), 7.75 (d, 1H), 8.90 (m, 1H), 8.98 (brd, 1H), 9.92 (brd, 1H);

$^{19}$F-NMR (d$_6$-DMSO) δ: −57.16

HRMS (ESI): calcd for $C_{31}H_{33}N_2O_3F_3S·HCl$ [M−Cl]$^+$ 571.2237, found 571.244

Example 21

Production of N-[(1R,2R)-1,2-diphenyl-2-(2-(4-methylbenzyloxy)ethylamino)-ethyl]-2-trifluoromethylbenzenesulfonamide ammonium chloride ruthenium monomer

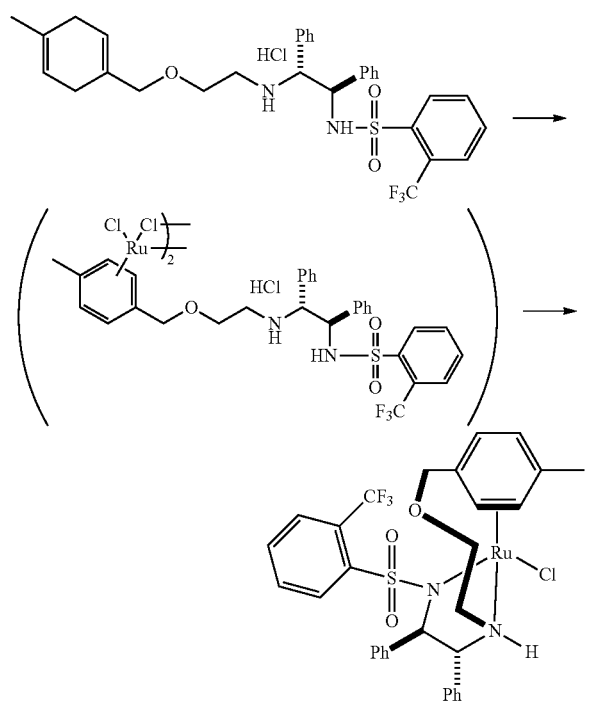

In a mixture solvent of 66 ml of 3-methoxypropanol and 22 ml of water, 5.0 g (8.25 mmol) of the diamine hydrochloride produced in Example 20 was dissolved, and 1.79 g (6.86 mmol) of ruthenium trichloride·trihydrate and 0.58 g (6.86 mmol) of sodium hydrogen carbonate were added thereto, followed by stirring at 120° C. for 2 hours. After 50 ml of 3-methoxypropanol was recovered, 75 ml of MIBK and 2.78 g (27.45 mmol) of triethylamine were added, followed by stirring at 60° C. for 1 hour. After 0.3 M hydrochloric acid was added, the resultant layers were separated from each other. The obtained organic layer was washed twice with water. Approximately 60 ml of the solvent was recovered, and crystallization was performed by adding 85 ml of heptane. The precipitated crystals were collected by filtration, and 4.60 g of the target Ru complex was obtained. Yield: 95.2%.

H-NMR (d$_6$-DMSO, 300 MHz) δ: 2.50 (s, 3H), 3.15-3.20 (m, 1H), 3.70-3.82 (m, 2H), 4.00 (m, 2H), 4.15 (m, 1H), 4.40 (m, 1H), 4.80 (m, 1H), 5.10 (d, 1H), 5.45 (d, 1H), 5.62 (d, 1H), 5.70 (d, 1H), 6.38 (d, 1H), 6.50-7.50 (m, 14H);

$^{19}$F-NMR (d$_6$-DMSO) δ: −58.45

HRMS (ESI): calcd for $C_{31}H_{30}ClN_2O_3F_3RuS$ [M+H]$^+$ 705.7034, found 705.0758

Example 22

2,4,6-Triisopropyl-N-((1S,2S)-2-(2-((4-methylcyclohexa-1,4-dienyl)methoxy)ethylamino)-1,2-diphenylethyl)benzenesulfonamide

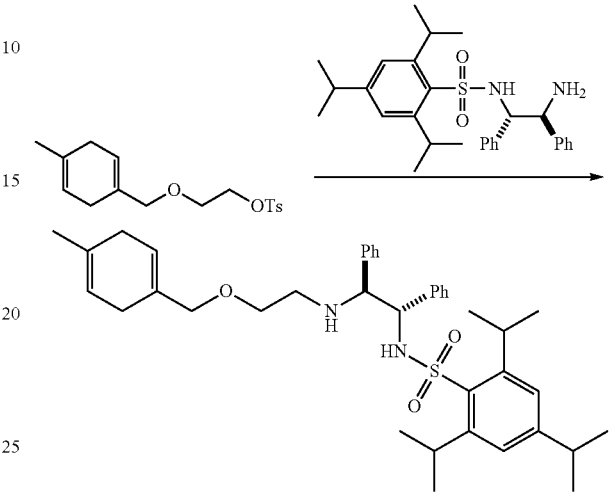

In 25 ml of toluene, 6.03 g (18.82 mmol) of the tosylate obtained in Example 17 was dissolved, and 2.43 g (18.82 mmol) of DIPEA and 9.00 g (18.80 mmol) of (S,S)-TIPPsDPEN were added thereto, followed by stirring at 135° C. for 13 hours. After that, the solvent was evaporated under reduced pressure, and the obtained residue was purified by silica gel column chromatography (toluene/ethyl acetate=20/1→15/1). Thus, 10.53 g of the title compound was obtained as a colorless oily substance. Yield: 89.0%.

H-NMR (CDCl$_3$, 300 MHz) δ: 1.06 (d, J=6.9 Hz, 3H), 1.21 (d, J=6.9 Hz, 3H), 1.87 (brs, 1H), 1.68 (s, 3H), 2.60 (brs, 4H), 2.71-2.48 (m, 2H), 3.52-3.34 (m, 2H), 3.55 (d, J=8.9 Hz, 1H), 3.77 (s, 2H), 3.95 (septet, J=6.7 Hz, 3H), 4.40 (d, J=8.9 Hz, 1H), 5.44 (m, 1H), 5.64 (m, 1H), 6.52 (brs, 1H), 7.28-6.74 (m, 12H);

HRMS (ESI): calcd for $C_{39}H_{53}N_2O_3S$ [M+H]+629.3771, found 629.3771

Example 23

Production of N-[(1S,2S)-1,2-diphenyl-2-(2-(4-methylbenzyloxy)ethylamino)-ethyl]-2,4,6-triisopropylbenzenesulfonamide ammonium chloride ruthenium monomer

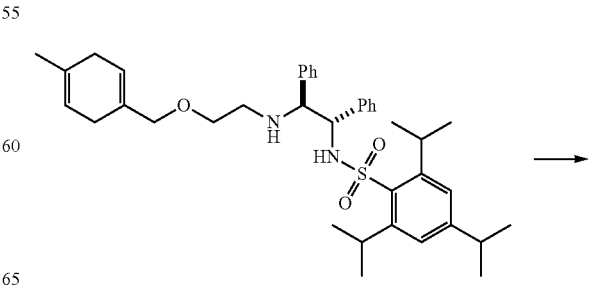

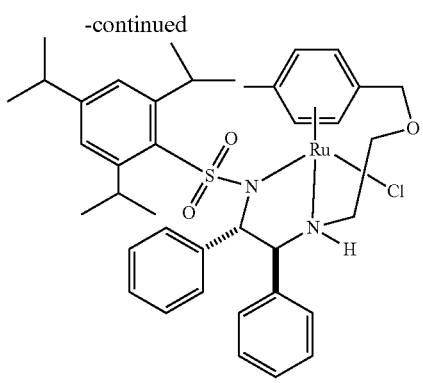

In 8 ml of methanol, 2.02 g (3.21 mmol) of the sulfonamide obtained in Example 22 was dissolved, and 0.67 g (6.42 mmol) of a 1N HCl (methanolic solution) was added thereto under ice-cooling, followed by stirring at room temperature for 20 minutes. After that, the solvent was evaporated under reduced pressure, and the obtained residue was dissolved in a mixture solvent of 30 ml of 3-methoxypropanol and 18 ml of water. To this solution, 0.72 g (2.75 mmol) of ruthenium trichloride.trihydrate was added, followed by stirring at 120° C. for 1 hour. The solvent was evaporated under reduced pressure, and 35 ml of IPA and 0.72 g (7.15 mmol) of triethylamine were added to the obtained residue, followed by stirring at 60° C. for 1 hour. The solvent was evaporated under reduced pressure, and the obtained residue was purified by silica gel column chromatography (chloroform/methanol=97/3→20/1). Thus, 1.28 g of the target Ru complex was obtained. Yield: 52.3%.

H-NMR (CD$_2$Cl$_2$, 300 MHz) δ: 1.0-1.2 (m, 18H), 1.70 (m, 1H), 2.41 (s, 3H), 2.60 (m, 1H), 3.05 (m, 1H), 3.35 (m, 1H), 3.68 (m, 1H), 3.75 (t, 1H), 3.85 (m, 2H), 4.18 (d, 1H), 4.25 (d, 1H), 4.85 (brs, 1H), 5.02 (d, 1H), 5.30 (d, 1H), 5.48 (d, 1H), 5.63 (d, 1H), 6.35 (d, 1H), 6.40-6.70 (m, 10H), 6.90-7.05 (m, 3H);

HRMS (ESI): calcd for C$_{39}$H$_{50}$N$_2$O$_3$SClRu [M+H]+ 763.2269, found 763.2257

Example 24

Production of 2-(cyclohexa-1,4-dienylmethoxy)ethanol

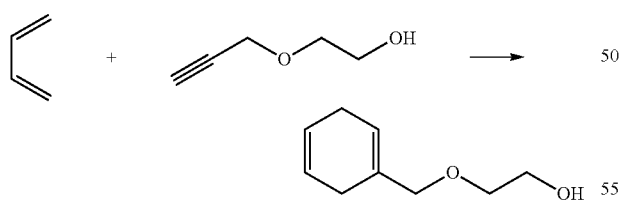

In 175 mL of dichloromethane, 1,2-bis(diphenylphosphino)ethane (1.73 g, 4.40 mmol), cobalt bromide (0.865 g, 4.00 mmol), and zinc iodide (4.2 g, 13.15 mmol) were dissolved, followed by stirring at 30° C. for 30 minutes. Then, 2-(propynyloxy)ethanol (8.94 g, 91.0 mmol) and butadiene (20% by weight toluene solution) (36.8 ml, 136.5 mmol) were added thereto, and then Bu$_4$NBH$_4$ (1.1 g, 4.3 mmol) was added. After stirring at 45° C. for 1 hour, the solvent was evaporated under reduced pressure, and the obtained residue was purified by silica gel column chromatography (hexane/ethyl acetate=5/1). Thus, 11.7 g of the title compound, an alcohol, was obtained as a colorless oily substance. Yield: 85.0%.

$^1$H NMR (CDCl$_3$, 300 MHz): δ 5.80-5.60 (m, 3H), 3.92 (s, 1H), 3.72 (t, 2H), 3.48 (t, 2H), 2.75-2.60 (m, 4H), 2.22 (brs, 1H)

Example 25

Production of 2-(cyclohexa-1,4-dienylmethoxy)ethyl 4-methylbenzenesulfonate

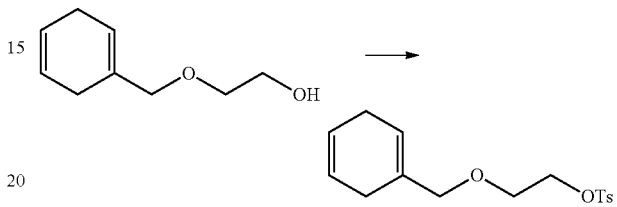

In 60 mL of toluene, 2-(cyclohexa-1,4-dienylmethoxy) ethanol (11.0 g, 71.3 mmol), triethylamine (8.66 g, 85.6 mmol), and 1-methylimidazole (7.0 g, 85.6 mmol) were dissolved. With cooling in an ice-bath, a toluene solution (40 ml) of p-toluenesulfonyl chloride (16.3 g, 85.6 mmol) was slowly added dropwise, followed by stirring at room temperature for 1 hour. Water was added thereto, and the resultant layers were separated from each other. The obtained organic layer was washed with 2 M hydrochloric acid and water. The solvent was evaporated under reduced pressure, and the obtained residue was purified by silica gel column chromatography (hexane/ethyl acetate=10/1→3/1). Thus, 21.0 g of the title compound, a tosylate, was obtained. Yield: 96%.

$^1$H NMR (CDCl$_3$, 300 MHz): δ 7.80 (d, 2H), 7.35 (d, 2H), 5.70-5.60 (m, 3H), 4.18 (t, 2H), 3.82 (s, 2H), 3.58 (t, 2H), 2.75-2.50 (m, 4H), 2.43 (s, 3H)

Example 26

Production of N-((1R,2R)-2-(2-(cyclohexa-1,4-dienylmethoxy)ethylamino)-1,2-diphenylethyl)-4-methylbenzenesulfonamide

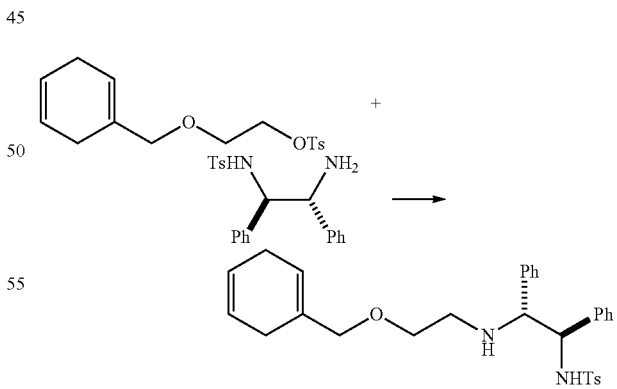

In 30 ml of toluene, 2-(cyclohexa-1,4-dienylmethoxy) ethyl 4-methylbenzenesulfonate (5.0 g, 16.21 mmol) was dissolved, and DIPEA (2.09 g, 16.21 mmol) and (R,R)-TsDPEN (5.94 g, 16.21 mmol) were added thereto, followed by stirring at 130° C. for 13 hours. After that, the solvent was evaporated under reduced pressure, and the obtained residue was purified by silica gel column chromatography (hexane/ ethyl acetate=2/1). Thus, 7.3 g of the title compound, a diamine, was obtained. Yield: 89.7%.

¹H NMR (CD₂Cl₂, 300 MHz): δ 7.40 (d, 2H), 7.20-6.90 (m, 12H), 6.30 (brs, 1H), 5.80-5.60 (m, 3H), 4.18 (d, 1H), 3.75 (s, 2H), 3.68 (d, 1H), 3.45-3.30 (m, 2H), 2.80-2.65 (m, 2H), 2.65-2.55 (m, 2H), 2.55-2.40 (m, 2H), 2.38 (s, 3H), 1.70 (brs, 1H)

HRMS (ESI): calcd for $C_{30}H_{35}N_2O_3S$ [M+H]⁺ 503.5363, found 503.2383

Example 27

Production of N-[(1R,2R)-1,2-diphenyl-2-(2-benzyloxy-ethylamino)-ethyl]-4-methylbenzenesulfonamide ammonium chloride ruthenium monomer (Benzene-Ts-DENEB)

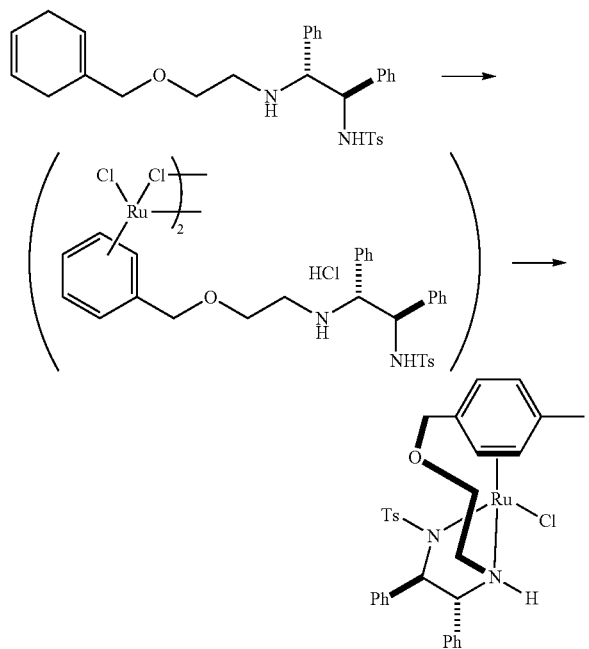

To N-((1R,2R)-2-(2-(cyclohexa-1,4-dienylmethoxy)ethylamino)-1,2-diphenylethyl)-4-methylbenzenesulfonamide (6.0 g, 11.1 mmol), 50 ml of 0.5 N HCl (methanolic solution) and 150 ml of methanol were added, followed by stirring at room temperature for 30 minutes. Then, the solvent was removed by an evaporator. To the obtained white solid, ruthenium trichloride.trihydrate (2.52 g, 9.63 mmol) and sodium hydrogen carbonate (0.8 g, 9.6 mmol) were added, and the mixture was dissolved in a mixture solvent of 86 ml of 3-methoxypropanol and 17 ml of water, followed by stirring at 120° C. for 1 hour. The solvent was evaporated under reduced pressure, and 97 ml of MIBK and triethylamine (3.9 g, 38.5 mmol) were added to the obtained residue, followed by stirring at 60° C. for 1 hour. After that, the solvent was removed under reduced pressure, and the obtained residue was purified by silica gel column chromatography. Thus, 5.28 g of the title compound, a ruthenium monomer, was obtained. Yield: 86.0%.

¹H NMR (CD₂Cl₂, 300 MHz): δ 7.20-6.55 (m, 14H), 6.35 (m, 1H), 5.95 (m, 1H), 5.83-5.78 (m, 3H), 4.80 (d, 1H), 4.40 (d, 1H), 4.35-4.20 (m, 1H), 4.10-4.00 (m, 2H), 3.85-3.75 (m, 2H), 3.45-3.20 (m, 2H), 2.25 (s, 3H)

HRMS (ESI): calcd for $C_{30}H_{31}ClN_2O_3RuS$ [M+H]⁺ 637.0860, found 637.0858

Example 28

Production of N-((1R,2R)-2-(2-(cyclohexa-1,4-dienylmethoxy)ethylamino)-1,2-diphenylethyl)methanesulfonamide

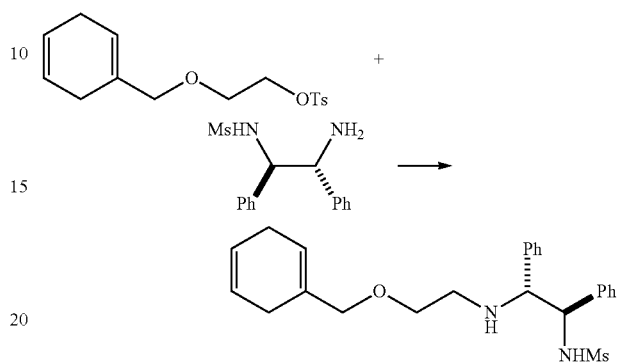

In 24 ml of toluene, 2-(cyclohexa-1,4-dienylmethoxy) ethyl 4-methylbenzenesulfonate (3.95 g, 12.8 mmol) was dissolved, and DIPEA (1.65 g, 12.8 mmol) and (R,R)-MsD-PEN (3.72 g, 12.8 mmol) were added thereto, followed by stirring at 130° C. for 23 hours. After that, the solvent was evaporated under reduced pressure, and the obtained residue was purified by silica gel column chromatography (hexane/ethyl acetate=3/1). Thus, 4.6 g of the title compound, a diamine, was obtained. Yield: 56.6%.

¹H NMR (CD₂Cl₂, 300 MHz): δ 7.30-7.18 (m, 10H), 6.08 (brs, 1H), 5.80-5.75 (m, 2H), 5.62-5.58 (m, 1H), 4.45 (m, 1H), 3.85 (d, 1H), 3.75 (s, 2H), 3.45-3.35 (m, 2H), 2.75-2.45 (m, 2H), 2.30 (s, 3H)

Example 29

Production of N-[(1R,2R)-1,2-diphenyl-2-(2-benzyloxy-ethylamino)-ethyl]methanesulfonamide ammonium chloride ruthenium monomer (Benzene-Ms-DENEB)

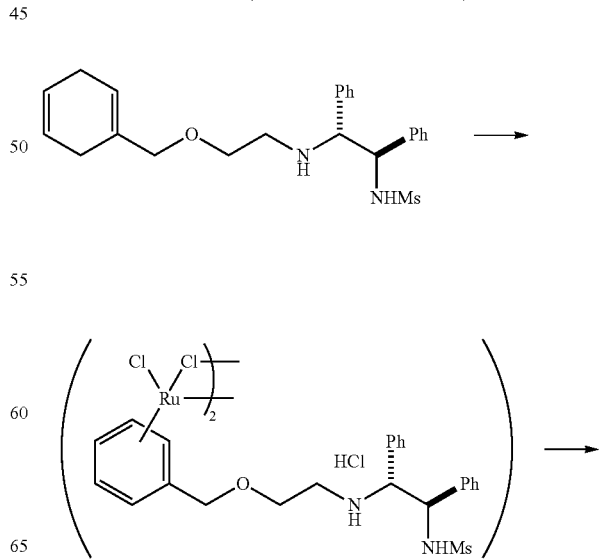

-continued

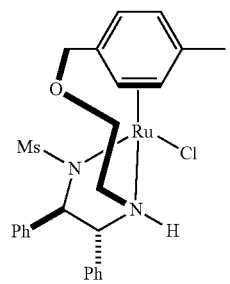

To N-((1R,2R)-2-(2-(cyclohexa-1,4-dienylmethoxy)ethylamino)-1,2-diphenylethyl)methanesulfonamide (4.5 g, 9.72 mmol), 45 ml of 0.5 N HCl (methanolic solution) and 120 ml of methanol were added, followed by stirring at room temperature for 30 minutes. Then, the solvent was removed by an evaporator. To the obtained white solid, ruthenium trichloride.trihydrate (2.31 g, 8.83 mmol) and sodium hydrogen carbonate (0.74 g, 8.8 mmol) were added, and the mixture was dissolved in a mixture solvent of 79 ml of 3-methoxypropanol and 16 ml of water, followed by stirring at 120° C. for 1 hour. The solvent was evaporated under reduced pressure, and 89 ml of MIBK and triethylamine (3.6 g, 35.3 mmol) were added to the obtained residue, followed by stirring at 60° C. for 1 hour. After that, the solvent was removed under reduced pressure, and the obtained residue was purified by silica gel column chromatography. Thus, 3.7 g of the title compound, a ruthenium monomer, was obtained. Yield: 68.0%.

$^1$H NMR (CD$_2$Cl$_2$, 300 MHz): δ 7.20-6.80 (m, 10H), 6.20 (m, 1H), 5.83 (m, 2H), 5.75 (m, 2H), 4.80 (d, 2H), 4.35 (d, 2H), 4.20 (brs, 1H), 4.10-3.90 (m, 2H), 3.80-3.50 (m, 2H), 3.50-3.15 (m, 2H), 2.43 (s, 3H)

HRMS (ESI): calcd for C$_{24}$H$_{27}$N$_2$O$_3$RuS [M–Cl]$^+$ 525.0780, found 525.0775

Example 30

Production of 5-hexynyl 4-methylbenzenesulfonate

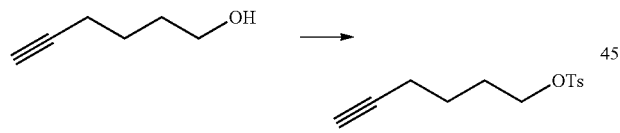

In 3 mL of toluene, 5-hexyn-1-ol (2.73 g, 27.82 mmol), triethylamine (3.38 g, 33.40 mmol), and 1-methylimidazole (2.74 g, 33.37 mmol) were dissolved. With cooling in an ice-bath, a toluene solution (12 ml) of p-toluenesulfonyl chloride (6.36 g, 33.36 mmol) was slowly added dropwise, followed by stirring at room temperature for 1 hour. Water was added thereto, and the resultant layers were separated from each other. The obtained organic layer was washed with 2 M hydrochloric acid, water, and saturated aqueous sodium chloride in this order. The solvent was evaporated under reduced pressure, and the obtained residue was purified by silica gel column chromatography (hexane/ethyl acetate=4/1). Thus, 7.0 g of the title compound, a tosylate, was obtained as a colorless oily substance. Yield: 99.7%.

$^1$H NMR (CDCl$_3$, 300 MHz): δ 7.79 (m, 2H), 7.35 (m, 2H), 4.05 (t, J=6.3 Hz, 2H), 2.45 (s, 3H), 2.17 (dt, J=2.7, 6.9 Hz, 2H), 1.93 (t, J=2.7 Hz, 1H), 1.83-1.74 (m, 2H), 1.62-1.51 (m, 2H);

HRMS (ESI): calcd for C$_{13}$H$_{17}$O$_3$S [M+H]+253.0893, found 253.08333

Example 31

Production of 4-(4-methylcyclohexa-1,4-dienyl)butyl 4-methylbenzenesulfonate and 3-(5-methylcyclohexa-1,4-dienyl)butyl 4-methylbenzenesulfonate

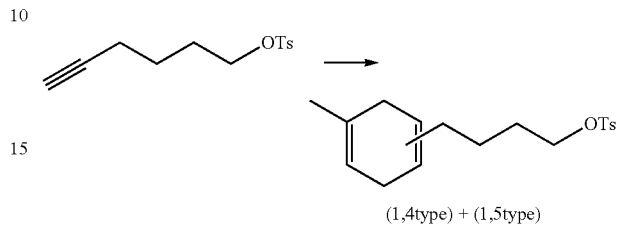

(1,4type) + (1,5type)

In 15 ml of THF, 1,2-bis(diphenylphosphino)ethane (0.25 g, 0.61 mmol), cobalt bromide (0.13 g, 0.59 mmol), zinc iodide (0.38 g, 1.19 mmol), and zinc (0.08 g, 1.24 mmol) were dissolved, followed by stirring at 70° C. for 15 minutes. After cooling to room temperature, isoprene (0.95 g, 13.86 mmol) was added. Then, the tosylate (3.00 g, 11.89 mmol) obtained in Example 20 was slowly added dropwise with cooling in a water bath. After stirring at 35° C. for 1 hour, the solvent was evaporated under reduced pressure, and the obtained residue was purified by silica gel column chromatography (hexane/ethyl acetate=5/1). Thus, 3.41 g of the title compound, a tosylate, was obtained as a colorless oily substance. Yield: 89.5% (isomer ratio: 1,4 type/1,5 type=73/27). Note that the following NMR spectrum data are those of the mixture of the two isomers.

$^1$H-NMR (CDCl$_3$, 300 MHz): δ 7.80-7.77 (m, 2H+2H'), 7.36-7.33 (m, 2H+2H'), 5.58-5.56 (m, 1H'), 5.51-5.49 (m, 1H'), 5.39-5.38 (m, 1H), 5.35-5.34 (m, 1H), 4.05-4.01 (m, 2H+2H'), 2.53 (brs, 4H), 2.45 (s, 3H+3H'), 2.05 (brs, 4H'), 1.99 (t, J=7.4 Hz, 2H), 1.91 (t, J=7.4 Hz, 2H), 1.76 (s, 3H'), 1.66 (s, 3H), 1.67-1.58 (m, 2H+2H'), 1.49-1.37 (m, 2H+2H');

HRMS (ESI): calcd for C$_{18}$H$_{24}$O$_3$SNa [M+Na]+343.1338, found 343.1342

Example 32

Hydrogen transfer reaction to acetophenone as substrate using N-[(1S,2S)-1,2-diphenyl-2-(4-(4-methylphenyl)butylamino)ethyl]-4-methylbenzenesulfonamide ammonium chloride ruthenium monomer and N-[(1S,2S)-1,2-diphenyl-2-(4-(3-methylphenyl)butylamino)ethyl]-4-methylbenzenesulfonamide ammonium chloride ruthenium monomer In a 25-ml Schlenk tube, 4.5 mg (0.00694 mmol, S/C=1000) of the ruthenium complexes produced in Example 6, acetophenone (0.82 g, 6.86 mmol), and 3.4 ml of a formic acid-triethylamine (5:2) azeotrope were mixed with each other, and a reaction was allowed to proceed at 60° C. for 5 hours. GC analysis of the reaction liquid showed that (S)-1-phenylethanol was formed with a conversion of 99.3% and 96.5% ee.

Example 33

Hydrogen transfer reaction to acetophenone as substrate using N-[(1S,2S)-1,2-diphenyl-2-(4-(4-methylphenyl)butylamino)ethyl]-methanesulfonamide ammonium chloride ruthenium monomer and N-[(1S,2S)-1,2-diphenyl-2-(4-(3- methylphenyl)butylamino)ethyl]-methanesulfonamide ammonium chloride ruthenium monomer In a 25-ml Schlenk tube, the ruthenium complexes (4.0 mg, 0.00694 mmol, S/C=1000) produced in Example 10, acetophenone (0.82 g, 6.86 mmol), and 3.4 ml of a formic acid-triethylamine (5:2) azeotrope were mixed with each other, and a reaction was allowed to proceed at 60° C. for 5 hours. GC analysis of the reaction liquid showed that (S)-1-phenylethanol was formed with a conversion of 99.4% and 94.8% ee.

Example 34

Hydrogen transfer reaction to acetophenone as substrate using N-[(1R,2R)-1,2-diphenyl-2-(2-benzyloxyethylamino)-ethyl]-4-methylbenzenesulfonamide ammonium chloride ruthenium monomer (Benzene-Ts-DENEB)

In a 25 ml-Schlenk tube, the ruthenium complex (3.2 mg, 0.005 mmol, S/C=1000) produced in Example 27, acetophenone (0.61 g, 5.0 mmol), and 2.5 ml of a formic acid-triethylamine (5:2) azeotrope were mixed with each other, and a reaction was allowed to proceed at 60° C. for 5 hours. GC analysis of the reaction liquid showed that (R)-1-phenylethanol was formed with a conversion 99.7% and 95.3% ee.

Example 35

Hydrogen transfer reaction to acetophenone as substrate using N-[(1R,2R)-1,2-diphenyl-2-(2-benzyloxyethylamino)-ethyl]met hanesulfonamide ammonium chloride ruthenium monomer (Benzene-Ms-DENEB)

In a 25-ml Schlenk tube, the ruthenium complex (2.8 mg, 0.005 mmol, S/C=1000) produced in Example 29, acetophenone (0.61 g, 5.0 mmol), and 2.5 ml of a formic acid-triethylamine (5:2) azeotrope were mixed with each other, and a reaction was allowed to proceed at 60° C. for 5 hours. GC analysis of the reaction liquid showed that (R)-1-phenylethanol was formed with a conversion 100% and 94.8% ee.

The invention claimed is:

1. A method for producing a compound of the following general formula (1):

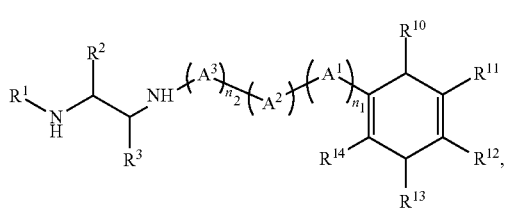

wherein $R^1$ represents an alkyl group having 1 to 10 carbon atoms; an alkanesulfonyl group having 1 to 10 carbon atoms and optionally substituted with a halogen atom; an arenesulfonyl group optionally substituted with an alkyl group having 1 to 10 carbon atoms, a halogenated alkyl group having 1 to 10 carbon atoms, or a halogen atom; an alkoxycarbonyl group having 2 to 11 carbon atoms in total; or a benzoyl group optionally substituted with an alkyl group having 1 to 10 carbon atoms, $R^2$ and $R^3$ each independently represent an alkyl group having 1 to 10 carbon atoms; a phenyl group optionally substituted with an alkyl group having 1 to 10 carbon atoms, an alkoxy group having 1 to 10 carbon atoms, or a halogen atom; or a cycloalkyl group having 3 to 8 carbon atoms, or $R^2$ and $R^3$ may together form a ring, $R^{10}$ to $R^{14}$ each independently represent a hydrogen atom, an alkyl group having 1 to 10 carbon atoms, an alkoxy group having 1 to 10 carbon atoms, or a trisubstituted alkylsilyl group, $A^1$ and $A^3$ represent methylene, $A^2$ represents an oxygen atom, and $n_1$ and $n_2$ are each independently 1 to 3, the method comprising:
reacting a compound of the following general formula (2):

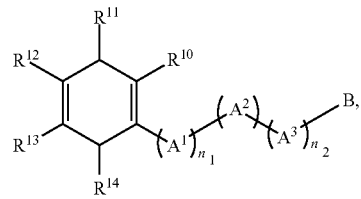

wherein $R^{10}$ to $R^{14}$, $A^1$ to $A^3$, $n_1$, and $n_2$ are the same as those defined in the general formula (1), and B represents a halogen atom, an alkanesulfonyloxy group, or an arenesulfonyloxy group, with a diamine compound of the following general formula (3):

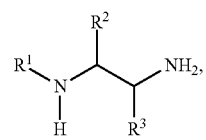

wherein $R^1$ to $R^3$ are the same as those defined in the general formula (1),
in the presence of a solvent selected from the group consisting of an aromatic hydrocarbon, halogenated aromatic hydrocarbon, ether, and aprotic polar solvent, and a base selected from the group consisting of an inorganic base and tertiary organic amine.

2. The production method according to claim 1, wherein the reaction of the compound of the general formula (2) is reacted with the diamine compound of the general formula (3) at a temperature of 100° C. to 200° C.

3. A compound of the following general formula (2):

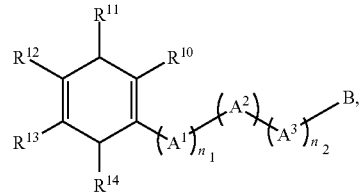

wherein $R^{10}$ to $R^{14}$ each independently represent a hydrogen atom, an alkyl group having 1 to 10 carbon atoms, an alkoxy group having 1 to 10 carbon atoms, or a trisubstituted alkylsilyl group, $A^1$ and $A^3$ represent methylene, $A^2$ represents an oxygen atom, B represents a halogen atom, an alkanesulfonyloxy group, or an arenesulfonyloxy group, and $n_1$ and $n_2$ are each independently 1 to 3.

* * * * *